(12) United States Patent
Li et al.

(10) Patent No.: US 8,939,930 B2
(45) Date of Patent: Jan. 27, 2015

(54) ACCURATE FLOW CONTROL IN DRUG PUMP DEVICES

(71) Applicant: MiniPumps, LLC., Pasadena, CA (US)

(72) Inventors: Po-Ying Li, Monrovia, CA (US);
Jonathan Lee, Montebello, CA (US);
Alice Lai, Pasadena, CA (US);
Yu-Chong Tai, Pasadena, CA (US);
Sean Caffey, Hawthorne, CA (US);
Stuart Long, Camarillo, CA (US)

(73) Assignee: MiniPumps, LLC, Pasadena, CA (US)

( * ) Notice: Subject to any disclaimer, the term of this patent is extended or adjusted under 35 U.S.C. 154(b) by 122 days.

(21) Appl. No.: 13/680,828

(22) Filed: Nov. 19, 2012

(65) Prior Publication Data

US 2013/0178792 A1    Jul. 11, 2013

(51) Int. Cl.
| A61M 5/172 | (2006.01) |
| A61M 5/168 | (2006.01) |
| A61M 5/145 | (2006.01) |
| A61M 5/155 | (2006.01) |

(52) U.S. Cl.
CPC .......... *A61M 5/172* (2013.01); *A61M 5/16854* (2013.01); *A61M 5/14566* (2013.01); *A61M 5/155* (2013.01)

USPC .............................. 604/67; 604/131; 604/151

(58) Field of Classification Search
CPC ............ A61M 5/172; A61M 5/16804; A61M 5/16854; A61M 5/16877; A61M 5/16886; A61M 2205/3334; A61M 5/14244; A61M 5/14276; A61M 31/002
USPC ............. 604/67, 131–151; 417/31, 38, 144.2, 417/148
See application file for complete search history.

(56) References Cited

U.S. PATENT DOCUMENTS

| 5,697,153 | A | * | 12/1997 | Saaski et al. ............. 29/890.128 |
| 5,993,414 | A | * | 11/1999 | Haller ......................... 604/93.01 |
| 2008/0125702 | A1 | * | 5/2008 | Blischak et al. ................. 604/67 |
| 2010/0114002 | A1 | * | 5/2010 | O'Mahony et al. .......... 604/6.09 |
| 2011/0275410 | A1 | * | 11/2011 | Caffey et al. ............... 604/891.1 |
| 2012/0046651 | A1 | * | 2/2012 | Beyer et al. ................ 604/891.1 |
| 2012/0283691 | A1 | * | 11/2012 | Barnes et al. ................. 604/500 |

* cited by examiner

*Primary Examiner* — Quynh-Nhu H Vu
(74) *Attorney, Agent, or Firm* — Morgan, Lewis & Bockius LLP

(57) ABSTRACT

The accuracy of drug delivery with drug pump devices may be improved by a combination of pump operation at high flow resistances and pump pressures, pressure-relief mechanisms, and sensor-based feedback for pump control.

20 Claims, 25 Drawing Sheets

ACCURATE FLOW CONTROL IN DRUG PUMP DEVICES

CROSS-REFERENCE TO RELATED APPLICATIONS

This application claims priority to and the benefit of, and incorporates herein by reference in their entirety, U.S. Provisional Patent Applications No. 61/561,565, filed on Nov. 18, 2011 and No. 61/704,974, filed on Sep. 24, 2012.

TECHNICAL FIELD

The invention relates generally to drug pump devices, and in various embodiments to electrolysis-driven piston pump devices.

BACKGROUND

The treatment of many diseases requires regular subcutaneous skin injections. For example, diabetes patients may need insulin injections following every meal and, in addition, a continuously administered low "basal" rate of insulin. The major technologies currently in use for frequent or continuous drug delivery are syringes, pre-filled pen injectors, and patient-filled portable drug pump devices. Each of these technologies has problems. For example, syringes, unless filled by a well-trained and skilled person (e.g., a health-care professional), can easily trap bubbles during the filling process, posing a risk to patient safety. Further, certain therapies require injection volumes greater than 1 ml; protein solutions, for example, often cannot be formulated with high concentration because the proteins precipitate in high concentrations, requiring large-volume injections instead. Large injection volumes, however, generally preclude the use of syringes because more than 1 ml can cause pain and swelling when injected at high rates of flow, such as with a syringe. Pre-filled pen injectors are advantageous in that they facilitate accurate manual insulin dosing using a pre-filled, bubble-free glass cartridge, which renders the priming process simple for the patient. However, since the injection is done manually, deficient patient compliance (e.g., improper injection timing and/or failure to follow the dosing prescription) is a major concern.

Portable drug pump devices can provide fully-controlled drug delivery; therefore, patient compliance is much improved. Decreased numbers of injections (once every three days, for example) and programmable dosing schedules may greatly enhance the patient's quality of life. In addition, many portable pump devices are provided in the form of patch pumps with low pump profiles, which can be attached to the patient's skin without interfering with daily activities such as showering, sleeping, and exercising. Controllable pump devices can, further, deliver drugs at slower rates than syringes and pen-injectors, thereby facilitating the injection of higher volumes of fluid (e.g., 1-10 ml) without causing discomfort or damage to local tissue; this is particularly important for viscous drug solutions (e.g., with viscosities of 35 cSt or higher). However, since these pumps are typically filled by patients, risks arise during the priming procedure. Improperly primed reservoirs may contain large air bubbles and cause the pump to inject too much air into the subcutaneous tissue, which is a serious safety matter. Moreover, many portable drug pump devices, including commercial insulin pumps, are driven by step motors (or similar components for rotating a gear). Step motors are known for their accurate rotational pitch control; however, their motion is discrete, not continuous. Therefore, the basal delivery flow provided by the step motor is also discrete. For example, basal rates in the range from 5 to 5000 nl/min—the typical dosage regime for insulin—are achieved by many systems with discrete 5 nl deliveries at rates between one delivery per hour and one thousand deliveries per hour. This discontinuous drug delivery is a major limitation of step-motor-driven insulin pumps.

Recently developed electrolytically driven piston pump devices that utilize a pre-filled glass (or polymer) vial in a pen-injection configuration solve many of the problems associated with prior technologies. They facilitate steady, continuous drug flow at a programmed rate, avoiding patient compliance issues. Additionally, the use of a pre-filled vial obviates the need for the patient to fill the drug reservoir, rendering the pump simpler to use and eliminating the risks of drug leakage due to improper filing and of introduction of particulates or foreign matter into the patient's subcutaneous tissue. However, providing controlled and accurate drug delivery still remains a challenge for pumps utilizing glass vials as drug reservoirs. This challenge arises largely from variable stiction/friction forces between the glass vial and the piston or plunger that drives the drug out of the vial. The resulting unstable flow resistance makes the drug flow difficult to control. It tends to cause basal drug delivery to suffer from varying flow rates despite constant driving pressure, and can render bolus delivery unpredictable from one bolus to the next. Accordingly, there is a need for improved flow control schemes and mechanisms to ensure constant, accurate, and predictable drug dosages for both basal and bolus deliveries.

SUMMARY

The present invention provides, in various embodiments, electrolytically driven drug pump devices with control mechanisms that facilitate accurate basal and/or bolus deliveries. In some embodiments, pump pressure generated in the electrolysis chamber is controlled by a feedback loop that adjusts the electrolysis rate based on measurements of pump pressure and/or the flow rate of the liquid drug. To reduce the effect of sudden changes in pump conditions (such as variations in friction forces) on the delivery rate, the device may include, downstream from the drug reservoir, a flow restrictor whose flow resistance dominates the overall flow resistance of the device; for example, a cannula, needle, or other exit member with a small inner diameter (e.g., of less than 50 µm) may serve as the flow restrictor, or the flow restrictor may be a separate component located, e.g., upstream of the exit member. Further, to achieve the desired flow rates (e.g., between 400 and 5000 nl/min) despite the high flow resistance, the pump may be operated at high driving pressures (e.g., pressures in excess of 5 psi and as much as 200 psi). Advantageously, within the high-pressure operational regime, pump pressure and flow rate are directly proportional over a wide range, allowing the flow rate to be accurately and precisely controlled (e.g., maintained at a specified constant value) based on measurements of the pump pressure in conjunction with knowledge of the flow resistance of the device.

For even higher accuracy in flow rate control and enhanced safety through sensor redundancy, a direct-measurement flow sensor may be used in combination with the pressure sensor, facilitating comparisons between the measured flow rate and a flow rate calculated from the measured pressure. In the event of a discrepancy between the two, a safety protocol may be initiated, e.g., to shut down pump operation. Alternatively, in some embodiments, the measured flow rate is used for pump control as long as it is within a specified margin of the calculated flow rate, and, otherwise, the measured flow rate is assumed to be erroneous and the calculated flow rate is substituted as the control parameter. (A "flow sensor," as used herein, is any sensor measuring the flow rate either directly, or indirectly via another physical quantity that has a known relationship to the flow rate. For example, a pressure sensor may function as a flow sensor in that the flow rate can be calculated from a pressure measurement, provided that the flow resistance is known (as described in more detail below). For clarity, flow sensors that measure the flow rate directly are herein referred to as "direct-measurement flow sensors.")

Accordingly, in one aspect, the invention provides a high-pressure drug pump device including a drug reservoir, an exit member for fluidically connecting the reservoir with a drug injection site, a flow restrictor for restricting fluid flow through the exit member, an electrolysis pump having a pump chamber in mechanical communication with the drug reservoir via an intervening displacement member (e.g., a piston or diaphragm), and control circuitry for operating the pump to generate pressure in the pump chamber to drive the displacement member toward the exit member and thereby force fluid from the reservoir through the exit member. The flow resistor has a flow resistance factor (defined further below as the flow resistance divided by the viscosity of the fluid) of at least $10^6$ $\mu l^{-1}$. The electrolysis pump is operable, and the control circuitry to configured to operate the pump, to exert a pressure of at least 2 psi, preferably at least 5 psi, on the displacement member. The circuitry and the flow restrictor, thus, cooperate to cause continuous fluid flow through the exit member at a constant flow rate in the range from about 400 nl/min to about 5 µl/min.

In some embodiments, the pump is operable to exert a pressure of at least 10 psi, at least 50 psi, at least 100 psi, or at least 200 psi. The flow restrictor may have a smallest inner diameter not exceeding 100 µm or, preferably, not exceeding 50 µm. Its length may be in the range from about 1 cm to about 15 cm. In some embodiments, the exit member includes the flow restrictor. In other embodiments, the flow restrictor is a separate component connected to the exit member (which may, e.g., be a needle or cannula). The flow resistance factor of the flow restrictor may be within a range that results in a substantially linear relationship between the pump pressure and the flow rate of fluid flow through the exit member.

The drug pump device may further include a pressure sensor disposed within the pump chamber for measuring a pressure therein, and/or a flow sensor disposed within the exit member. The circuitry for operating the pump may be configured to adjust an electrolysis current supplied to the electrolysis electrodes based on a comparison of that measured pressure or flow rate with a target pressure or target flow rate so as to cause fluid flow at a target flow rate so as to cause fluid flow at a constant specified flow rate. In certain embodiments, the pump includes both pressure and flow sensors, and the circuitry is configured to calculate a flow rate from the measured pressure, compare the calculated flow rate with the measured flow rate, and adjust the electrolysis current supplied to the electrodes based on either the measured or the calculated flow rate, depending on a discrepancy between the two. For example, if the measured flow rate if it is within 5% of the calculated flow rate, the pump may adjust the electrolysis current based on the measured flow rate; otherwise, it may base the current adjustment on the calculated flow rate. This arbitration scheme serves to operate the pump to generate a pressure that causes continuous fluid flow through the exit member at a target flow rate.

In certain embodiments, the drug reservoir of the device is formed inside a vial, and the displacement member includes a piston movably disposed within the vial. The electrolysis pump may include an electronics module mounted to an end of the vial and forming the pump chamber between the piston and the electronics module. The pump chamber may be sealed, at a wall formed by the electronics module, using an O-ring seated on top of a rim of the vial and within a circumferential recess of the electronics module. The electronics module may be removable and reusable in a separate drug pump device.

BRIEF DESCRIPTION OF THE DRAWINGS

The foregoing will be more readily understood from the following detailed description of the invention, in particular, when taken in conjunction with the drawings, in which.

DETAILED DESCRIPTION

Figure 1:
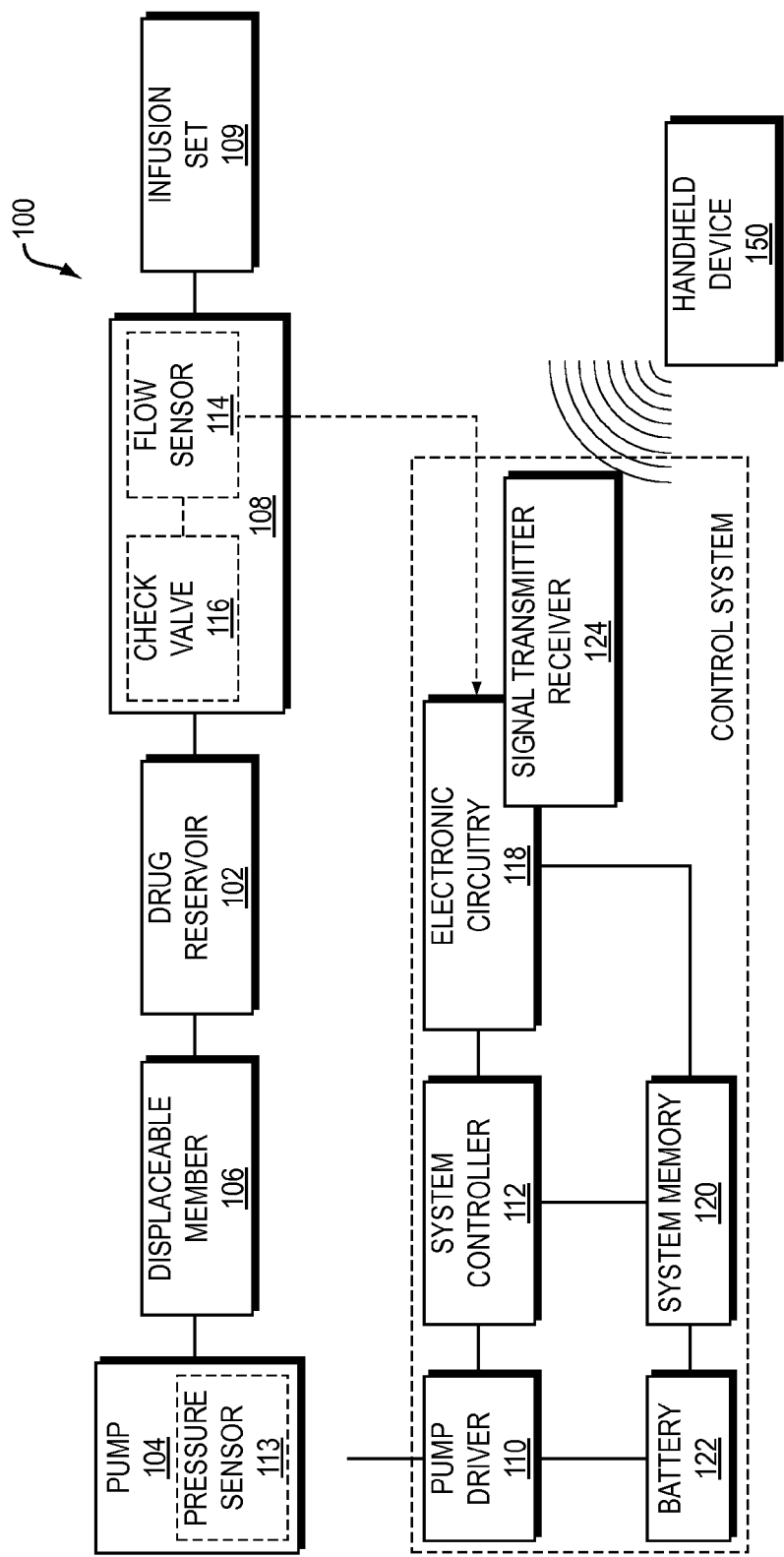
FIG. 1 is a block diagram illustrating the various functional components of electrolytic drug pump devices in accordance with various embodiments.

FIG. 1 illustrates, in block diagram form, the main functional components of a drug pump device 100 in accordance with various embodiments of the present invention. In general, the pump device 100 includes a drug reservoir 102 that interfaces with an electrolysis pump 104 via a displaceable member 106. The displaceable member 106 may be, for example, a piston, diaphragm, bladder, or plunger. In use, the drug reservoir 102 is filled with medication in liquid form, and pressure generated by the pump 104 moves or expands the displaceable member 106 so as to push the liquid drug out of the reservoir 102. A cannula, needle, or other exit member 108 connected to an outlet of the drug reservoir 102 conducts the liquid to an infusion set 109. The infusion set 109 may include a catheter fluidically connected to the cannula 108 for delivering the drug to a subcutaneous tissue region. A lancet and associated insertion mechanism may be used to drive the catheter through the skin. Alternatively, the infusion set 109 may include another type of drug-delivery vehicle, e.g., a sponge or other means facilitating drug absorption through the skin surface.

The electrolysis pump 104 generally includes an electrolyte-containing chamber (hereinafter also referred to as the "pump chamber") and, disposed in the chamber, one or more pairs of electrodes that are driven by a direct-current power source to break the electrolyte into gaseous products. Suitable electrolytes include water and aqueous solutions of salts, acids, or alkali, as well as non-aqueous ionic solutions. The electrolysis of water is summarized in the following chemical reactions:

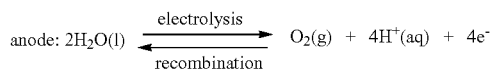

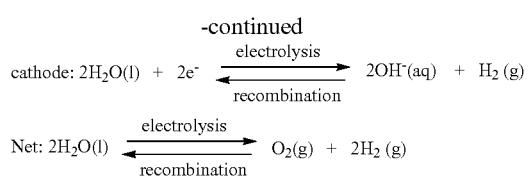

The net result of these reactions is the production of oxygen and hydrogen gas, which causes an overall volume expansion of the drug chamber contents. Gas evolution occurs even in a pressurized environment (reportedly at pressures of up to 200 MPa, corresponding to about 30,000 psi). As an alternative (or in addition) to water, ethanol may be used as an electrolyte, resulting in the evolution of carbon dioxide and hydrogen gas. Ethanol electrolysis is advantageous due to its greater efficiency and, consequently, lower power consumption, compared with water electrolysis. Electrolysis pumps in accordance with several embodiments are described in detail further below.

The pressure generated by the drug pump 104 may be regulated via a pump driver 110 by a system controller 112 (e.g., a microcontroller). The controller 112 may set the drive current and thereby control the rate of electrolysis, which, in turn, determines the pressure. In particular, the amount of gas generated is proportional to the drive current integrated over time, and can be calculated using Faraday's law of electrolysis. For example, creating two hydrogen and one oxygen molecule from water requires four electrons; thus, the amount (measured in moles) of gas generated by electrolysis of water equals the total electrical charge (i.e., current times time), multiplied by a factor of ¾ (because three molecules are generated per four electrons), divided by Faraday's constant.

The system controller 112 may execute a drug-delivery protocol programmed into the drug pump device 100, and may be responsive to one or more sensors 113, 114 that measure an operational parameter of the device 100, such as the pressure in the pump chamber 104 or the flow rate through (or pressure in) the cannula 108. For example, the controller 112 may adjust the current supplied to the electrolysis electrodes based on the pressure inside the pump chamber to achieve a target pressure. The target pressure, in turn, may be calculated based on a desired flow rate, using a known relationship between flow rate and pressure (as determined, e.g., by calibration). Due to the low cost of pressure sensors (such as, e.g., MEMS sensors as used in the automotive industry), this option is particularly advantageous for pumps designed for quick drug delivery. Indeed, two or more pressure sensors 113 may be placed in the pump chamber to simultaneously monitor pressure therein; this redundancy provides additional feedback to the controller 112, improves accuracy of information, and serves as a backup in case of malfunction of one of the sensors. Alternatively, the rate of drug flow out of the reservoir 102 may be measured directly and in real-time, using a flow sensor 114 integrated in the exit member 108 in a conventional manner. The total delivered dose can be computed by integrating the flow rate over time, and may serve as a control parameter for the electrolysis current.

In some embodiments, a pressure sensor 113 inside the pump chamber is used in combination with a flow sensor 114 in the cannula to increase the accuracy and precision of the feedback control loop. The use of multiple sensors also ensures that, in case the flow sensor 114 fails, the pressure sensor 113 would be able to detect high drug delivery rates, and shut the pump 104 down to avoid administration of an overdose to the patient or damage to the pump device. Conversely, the combination of flow and pressure sensors 114, 113 can also detect a violation in the drug reservoir 102 if pressure is measured in the pump chamber but no flow is measured in the cannula 108, indicating a potential leak. In general, the sensors used to measure various pump parameters may be flow, thermal, time of flight, pressure, or other sensors known in the art, and may be fabricated (at least in part) from parylene—a biocompatible, thin-film polymer. The cannula 108 may also include a check valve 116 that prevents accidental drug delivery and backflow of liquid into the drug reservoir 112; like the sensor 114, the check valve 116 may be made of parylene. In other embodiments, silicon or glass are used in part for the flow sensor 114 and valve 116 construction.

The drug pump device 100 may include electronic circuitry 118 (which may, but need not, be integrated with the system controller 112) for conditioning and further processing the sensor signal(s) and, optionally, providing pump status information to a user by means of LEDs, other visual displays, vibrational signals, or audio signals. In addition to controlling the drug pump 104, the controller 112 may be used to control other components of the drug pump system; for example, it may trigger insertion of the lancet and catheter. The system controller 112 may be a microcontroller, i.e., an integrated circuit including a processor core, memory (e.g., in the form of flash memory, read-only memory (ROM), and/or random-access memory (RAM)), and input/output ports. The memory may store firmware that directs operation of the drug pump device. In addition, the device may include read-write system memory 120. In certain alternative embodiments, the system controller 112 is a general-purpose microprocessor that communicates with the system memory 120. The system memory 120 (or memory that is part of a microcontroller) may store a drug-delivery protocol in the form of instructions executable by the controller 112, which may be loaded into the memory at the time of manufacturing, or at a later time by data transfer from a hard drive, flash drive, or other storage device, e.g., via a USB, Ethernet, or firewire port. In alternative embodiments, the system controller 112 comprises analog circuitry designed to perform the intended function.

The pump driver 110, system controller 112, and electronic circuitry 118 may be powered, via suitable battery electronics, by a battery 122. Suitable batteries 122 include non-rechargeable lithium batteries approximating the size of batteries used in wristwatches, as well as rechargeable Li-ion, lithium polymer, thin-film (e.g., Li-PON), nickel-metal-hydride, and nickel cadmium batteries. Other devices for powering the drug pump device 100, such as a capacitor, solar cell or motion-generated energy systems, may be used either in place of the battery 122 or supplementing a smaller battery. This can be useful in cases where the patient needs to keep the drug-delivery device 100 on for several days or more.

In certain embodiments, the drug pump device 100 includes, as part of the electronic circuitry 118 or as a separate component, a signal receiver 124 (for uni-directional telemetry) or a transmitter/receiver 124 (for bi-directional telemetry) that allows the device to be controlled and/or re-programmed remotely by a wireless handheld device 150, such as a customized remote control or a smartphone. In certain embodiments, the handheld device 150 and pump device 100 communicate over a (uni- or bidirectional) infrared (IR) link, which may utilize one or more inexpensive IR light-emitting diodes and phototransistors as transmitters and receivers, respectively. Communication between the drug pump device 100 and the handheld device 150 may also occur at radio frequencies (RF), using, e.g., a copper coil antenna as the transmitter/receiver component 124.

The drug-delivery device 100 may be manually activated, e.g., toggled on and off, by means of a switch integrated into the pump housing. In some embodiments, using the toggle switch or another mechanical release mechanism, the patient may cause a needle to pierce the enclosure of the drug reservoir 102 (e.g., the septum of a drug vial, as explained below with respect to FIG. 2) to establish a fluidic connection between the reservoir 102 and the cannula 108; priming of the pump can then begin. Coupling insertion of the needle into the reservoir 102 with the activation of the pump device ensures the integrity of the reservoir 102, and thus protects the drug, up to the time when the drug is injected; this is particularly important for pre-filled drug pump devices. Similarly, the lancet and catheter of the infusion set 109 may be inserted by manually releasing a mechanical insertion mechanism. In some embodiments, insertion of the lancet and catheter automatically triggers electronic activation of a pump, e.g., by closing an electronic circuit. Alternatively, the pump and/or insertion set may be activated remotely by wireless commands.

The functional components of drug pump devices as described above may be packaged and configured in various ways. In certain preferred embodiments, the drug pump device is integrated into a patch adherable to the patient's skin. Suitable adhesive patches are generally fabricated from a flexible material that conforms to the contours of the patient's body and attaches via an adhesive on the backside surface that contacts a patient's skin. The adhesive may be any material suitable and safe for application to and removal from human skin. Many versions of such adhesives are known in the art, although utilizing an adhesive with gel-like properties may afford a patient particularly advantageous comfort and flexibility. The adhesive may be covered with a removable layer to preclude premature adhesion prior to the intended application. As with commonly available bandages, the removable layer preferably does not reduce the adhesion properties of the adhesive when removed. In some embodiments, the drug pump device is of a shape and size suitable for implantation.

The various components of the drug pump device may be held within a housing mounted on the skin patch. The device may either be fully self-contained, or, if implemented as discrete, intercommunicating modules, reside within a spatial envelope that is wholly within (i.e., which does not extend beyond in any direction) the perimeter of the patch. The housing may provide mechanical integrity and protection of the components of the drug pump device 100, and prevent disruption of the pump's operation from changes in the external environment (such as pressure changes). The control system components 110, 112, 118, 120, 122 may be mounted on a circuit board, which may be flexible and/or may be an integral part of the pump housing. In some embodiments, the control system components are integrated with the electrolysis electrodes into self-contained unit.

Drug pump devices 100 in accordance herewith may be designed for single or repeated use. Multi-use pumps generally include a one-way check valve and a flow sensor, as described above, in the cannula. Further, the drug reservoir of a multi-use pump may be refillable via a refill port, using, e.g., a standard syringe. In some embodiments, the drug pump device 100 is removed from the patient's skin for re-filling. The patient may, for example, place the drug pump device 100 and cartridge containing the new drug into a home refill system, where the pump device and cartridge may be aligned using, e.g., a press-machine mechanism. The patient may then press a button to trigger automatic insertion of a needle that draws liquid drug from the cartridge to the cannula in order to activate the electronics and begin priming the pump.

The electrolysis pump 104 and drug reservoir 102 may be arranged within the device 100 in different ways, the two most common being a piston-pump configuration, in which the pump chamber and reservoir are formed within an elongated vial and separated by a piston movable along the axis of the vial, and the diaphragm-pump configuration, in which the reservoir is disposed on top of the pump chamber and separated therefrom by a flexible diaphragm. Both configurations are described in detail in U.S. patent application Ser. No. 13/091,047, filed on Apr. 20, 2011, which is hereby incorporated herein by reference in its entirety.

Figure 2A:
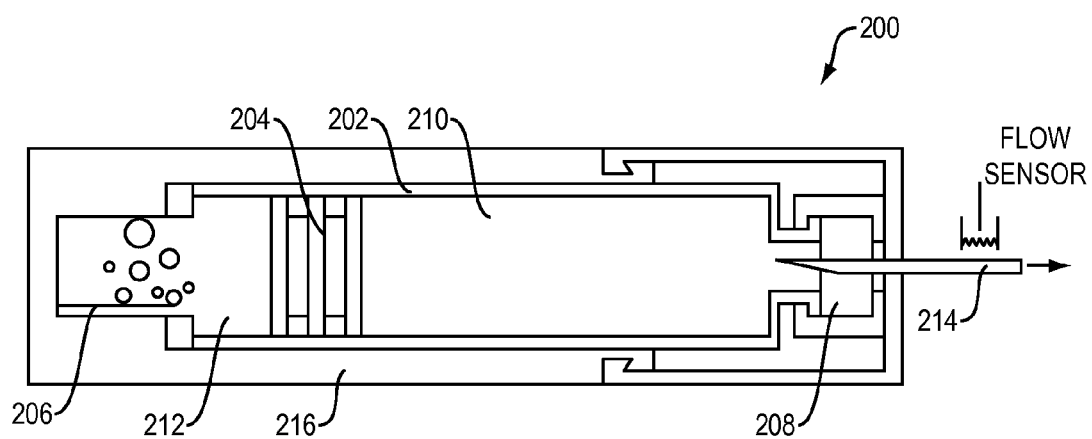
FIG. 2A is a schematic side view of a piston pump device in accordance with various embodiments.

FIG. 2A schematically illustrates an exemplary piston pump device 200. The pump device 200 includes a cylindrical (or, more generally, tubular) vial 202 with a piston 204 movably positioned therein and an electrolysis electrode structure 206 mounted to one end. A septum 208 may be disposed at the other end to seal the vial 202. Both the piston 204 and the septum 208 may be made of an elastomeric polymer material, such as a synthetic or natural rubber; in some embodiments, silicone rubber (i.e., polydiorganosiloxane, e.g., polydimethylsiloxane) is used. The piston 204 separates the interior of the vial 202 into a drug reservoir 210 and a pump chamber 212. In use, a needle 214 pierces the septum 208 to allow fluid egress from the drug reservoir 210; a cannula (not shown) connected to the needle 214 may conduct the fluid to the infusion set (not shown). The piston pump device 200 is enclosed in a protective housing 216, e.g., made of a hard plastic.

Figure 2B:
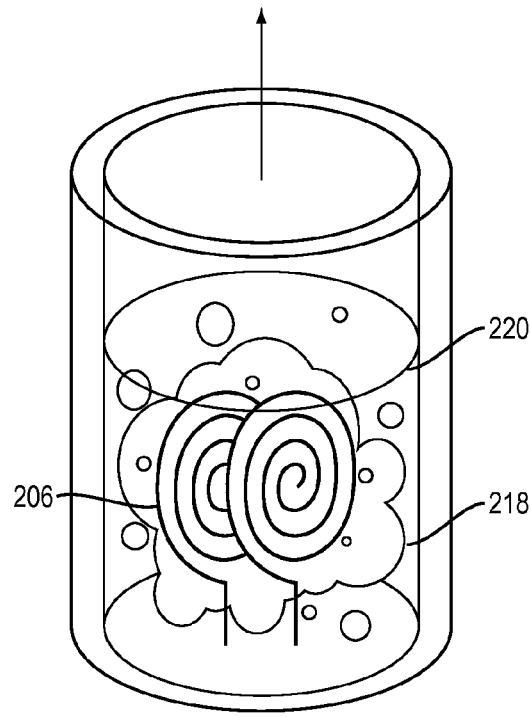
FIG. 2B is a schematic isometric view of an electrolysis pump chamber in accordance with various embodiments.

The electrodes 206 may be made of any suitable metal, such as, for example, platinum, titanium, gold, or copper, and may form a pair of parallel wires or plates. Alternatively, to improve electrolysis efficiency, the electrodes can have non-traditional shapes. For example, they may be interdigitated, or individually wound up into a spiral configuration (and oriented so as to face each other) as illustrated in FIG. 2B. Further, as shown, the electrodes 206 may be embedded in a hydrophilic absorbent material 218 (e.g., a cotton ball) that ensures continuous contact with the electrolyte 220. This solves a problem frequently encountered with conventional electrolysis pumps, in which the electrodes are simply submerged in liquid electrolyte: as gaseous electrolysis products are generated, they push the piston towards the outlet end of the drug reservoir, thereby increasing the volume of the electrolysis chamber, which causes a decrease in the level of the electrolyte. Depending on the orientation of the device, one or both electrodes may, as a result, gradually emerge from the electrolyte and become surrounded by the gas, eventually forming an open circuit and, thus, causing the electrolysis reaction to cease. This problem can be avoided in various ways, one of which is to surround the electrodes with a hydrophilic absorbent material such as (but not limited to) a hydrogel, cotton ball, sponge, or super-absorbent polymer. The electrolyte stays inside the hydrophilic absorbent material, which efficiently expels the generated gas and keeps the electrodes replenished with electrolyte.

The vial 202 may be fabricated from a glass, polymer, or other materials that are inert with respect to the stability of the drug and, preferably, biocompatible. Polymer vials, e.g., made of polypropylene or parylene, may be suitable for certain drugs that degrade faster when in contact with glass, such as protein drugs. For many other drugs, glass is the preferred material. Glass is commonly used in commercially available and FDA-approved drug vials and containers from many different manufacturers. As a result, there are well-established and approved procedures for aseptically filling and storing drugs in glass containers, which may accelerate the approval process for drug pump devices that protect the drug in a glass container, and avoid the need to rebuild a costly aseptic filling manufacturing line. Using glass for the reservoir further allows the drug to be in contact with similar materials during shipping. Suitable glass materials for the vial may be selected based on the chemical resistance and stability as well as the shatterproof properties of the material. For example, to reduce the risk of container breakage, type-II or type-III soda-lime glasses or type-I borosilicate materials may be used.

To enhance chemical resistance and maintain the stability of enclosed drug preparations, the interior surface of the vial may have a specialized coating. Examples of such coatings include chemically bonded, invisible, ultrathin layers of silicon dioxide or medical-grade silicone emulsions. In addition to protecting the chemical integrity of the enclosed drugs, coatings such as silicone emulsions may provide for lower and more uniform friction between the piston and vial.

In certain embodiments, the piston pump device 200 is manufactured by fitting a conventional, commercially available glass or polymer drug vial, which may already be validated for aseptic filling, with the piston 204 and electrolysis pump components. A screw-in needle cassette may be placed over the septum 208, and a mechanical actuation mechanism may serve to screw the cassette into the vial 202 such that the cassette needle 214 punctures the septum 208 and establishes a connection with the cannula at the time the patient desires to use the pump. To accommodate the electrolysis pump, the vial 202 is, in some embodiments, longer than typical commercially available vials, but maintains all other properties such that validated filling methods and the parameters of existing aseptic filling lines need not be changed. The drug pump device may be furnished with a prefilled vial. If a glass vial is used, the drugs can be stored in the pump device for long-term shelf life without the need to change the labeling on the drug.

Figure 3A:
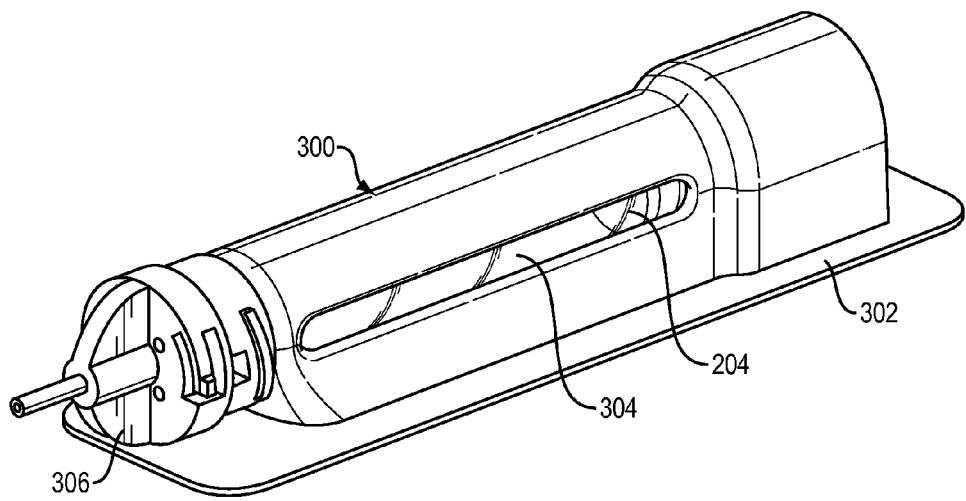
FIGS. 3A-3C are isometric, side, and exploded views, respectively, of a piston pump device in accordance with various embodiments.
Figure 3B:
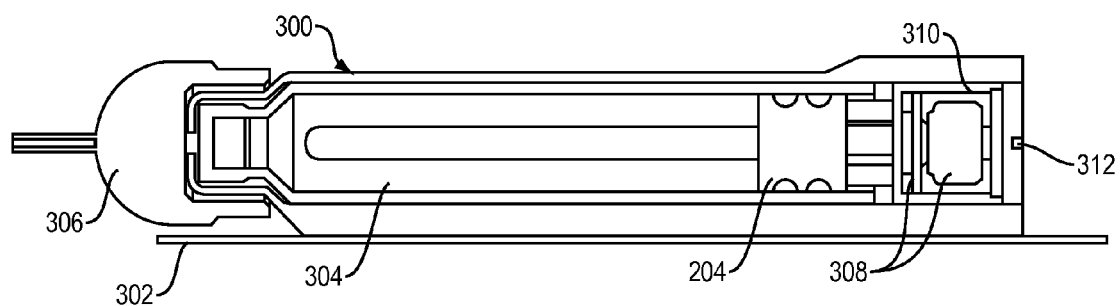
Figure 3C:
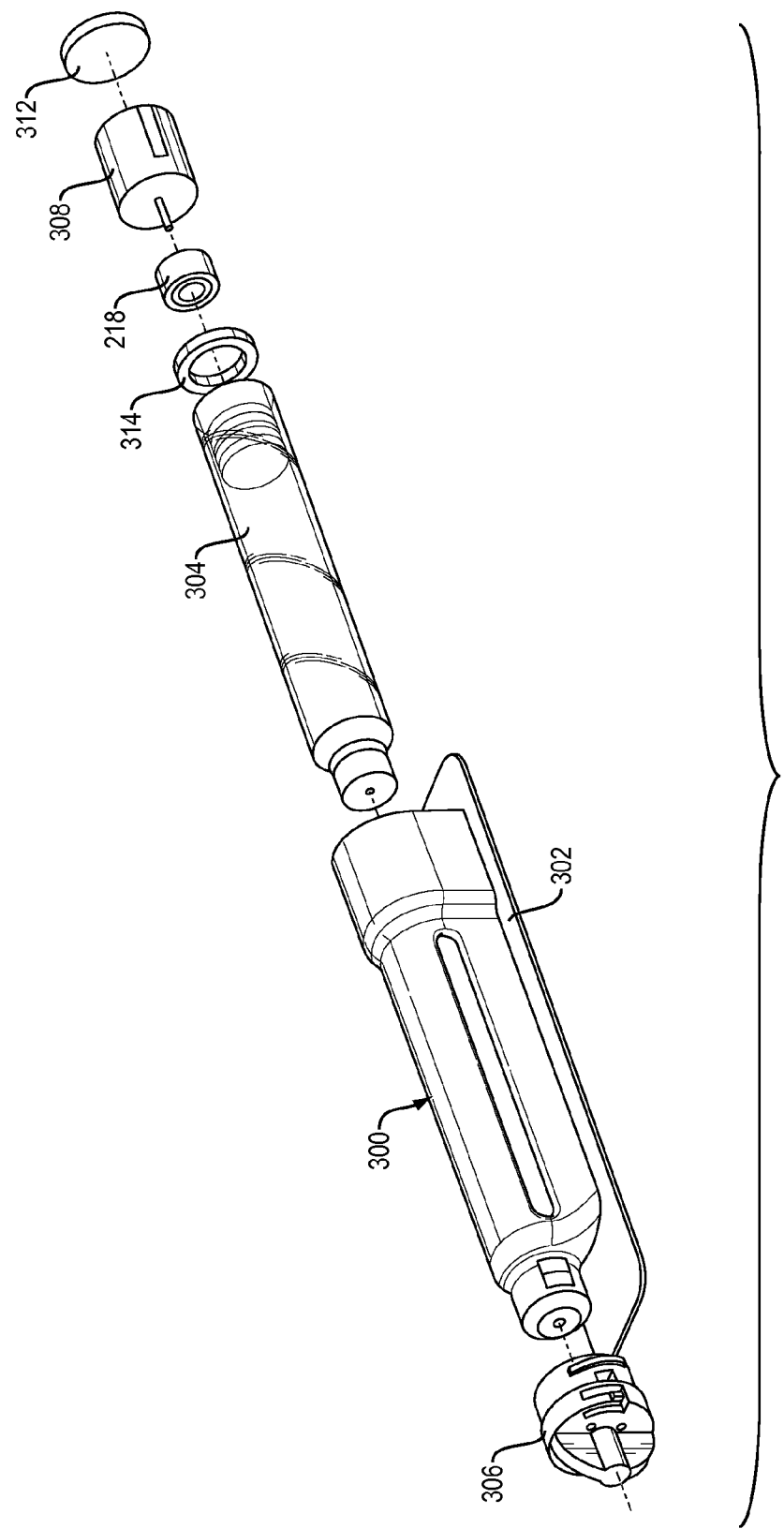

FIGS. 3A-3C show a representative piston pump design. In the illustrated embodiment, a pump case 300 integrated with a skin patch 302—i.e., affixed to the patch 302 by, e.g., an adhesive or manufactured with the patch as a single integrated structure—is adapted to axially receive a prefilled drug cartridge 304 through an opening in the back of the case 300. An off-the-shelf lancet set 306 can be mounted to the front end of the case 300 and used to establish a fluid connection between the cartridge 304 and an injection catheter. The electrolysis electrodes, electronics, and battery are integrated into a single module 308, enclosed in a plastic housing 310 from which the electrodes protrude at one end, to simplify assembly. A back-screw 312 may be used to secure the electrode/electronics/battery module 308 inside the pump case, with the module housing 310 abutting the end of the glass cartridge 304. A rubber O-ring 314 can be used to provide a seal between the end of the glass cartridge 304 and the electrode/electronics/battery module 310 in order to ensure the integrity of the electrolysis chamber formed therebetween.

Figure 4A:
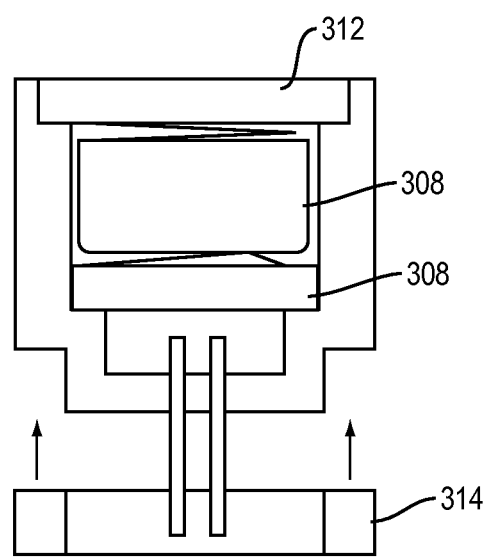
FIGS. 4A-4D are schematic side views of an electrode/electronics/battery module and its assembly into the pump device of FIGS. 3A and 3B in accordance with various embodiments.
Figure 4B:
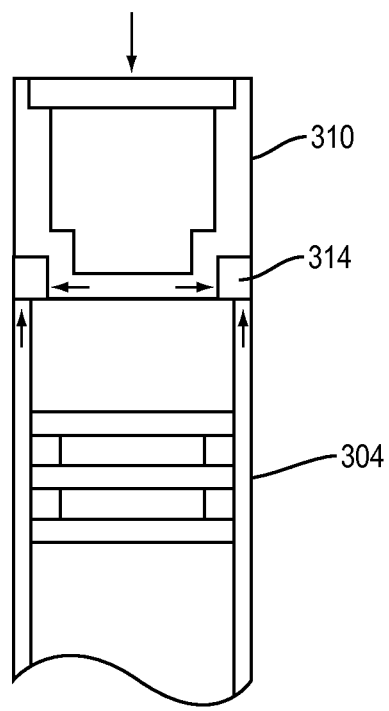

As discussed further below, various pump devices in accordance herewith are designed for operation at higher pump pressures than conventional drug pump devices (e.g., pressures in excess of 5 psi, 10 psi, 20 psi, 50 psi, 100 psi, or 200 psi). Accordingly, the case and pump connections for these devices are configured to withstand such high internal pressure without causing any leakage. A key component of high-pressure pump case designs in accordance with various embodiments is the electrode/electronics/battery housing 310. As illustrated in FIGS. 4A and 4B, this housing 310 seals against the O-ring 314 between the drug vial 304 and the housing 310. The bottom wall 320 of the housing 310 may include a circumferential recess 322 into which the O-ring 314 is placed; the recess 322 is sized such that the O-ring 314 is securely seated on top of the rim 324 of the drug vial 304 when the housing 310 is mated to the drug vial 304. In this configuration, the O-ring 314 is prevented from slipping inward, i.e., into the interior of the pump chamber, while the back screw 312 is tightened forward in the assembly process. As a result, much higher pressures can be generated in the pump chamber without causing leakage. The housing 310 may be secured to the vial 304 via any of a variety of conventional engagement mechanisms. For example, the housing 310 may extend over the vial 304 and be connected thereto around an inner surface by an adhesive, or the vial 304 may be threaded, or have a threaded collar adhered thereto.

Figure 4C:
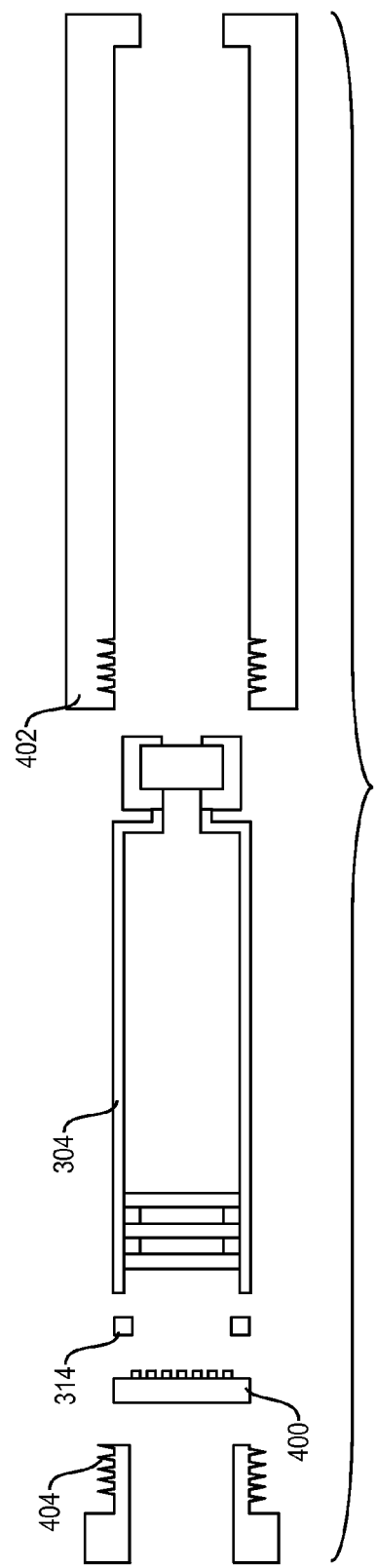
Figure 4D:
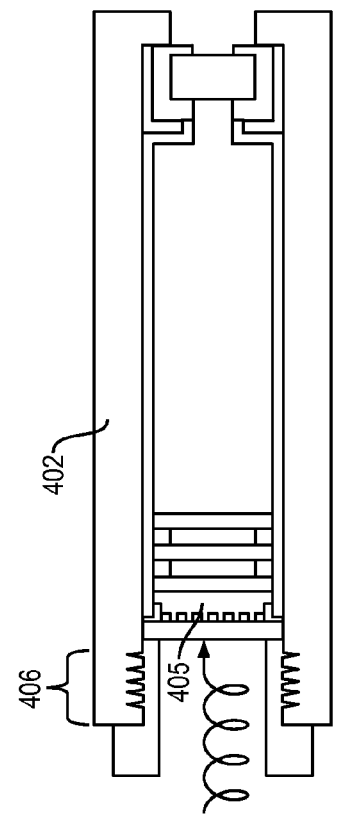

FIGS. 4C and 4D illustrate how the vial 304 and electrode module 400 can be secured and sealed within a pump case 402 using a compression nut 404. Although the electrode module 400 is herein illustrated simply as an electrode structure on a substrate, the embodiment can be straightforwardly modified to include, instead, an electrode/electronics/battery module 308 as shown in FIGS. 3A-3C. As in FIGS. 4A and 4B, the pump chamber 405 is formed in the back-end of the vial 304 between the piston 204 and the electrode module 400, and is sealed by an O-ring 314 (or other gasket) placed between the rim of the vial 304 and the electrode module 400. The pump case 402 is sized so as to fully accommodate therein the vial 304 and electrode module 400, extending beyond the assembly at the back end. The overhanging portion 406 of the pump case 402 is threaded at its interior surface, allowing the compression nut 404 to be screwed into the pump case 402 to apply a compression force on the O-ring for sealing the pump chamber 405.

In many wearable pump designs, the battery and electronics (which can optionally include wireless modules such as bluetooth or zigbee) represent components that are expensive to produce and/or dangerous to the environment (due to the materials used); these drawbacks are, however, ameliorated if the battery and electronics can be recharged or reprogrammed and, thus, reused. In certain embodiments, the battery (or batteries) and electronics of the drug pump device can be packaged into a battery and electronics module (BEM) (e.g., the module 308) that can be reused many times for multiple infusion pumps. In a preferred embodiment, the BEM can be inserted or snapped (with an electrical connection) into the pump by the patient before use, and removed at the end of the infusion. In addition to rendering the use of drug pump devices more economical, this reuse delays or avoids the disposal of environmentally damaging materials (e.g., batteries made of nickel metal hydride, liPON, lithium ion, or lithium polymer) in landfills. Moreover, a removable BEM facilitates sterilizing the pump by methods such as ion beam or gamma irradiation, which damage traditional electronics, and adding the electronics after sterilization. In some embodiment, a charging/reprogramming station with a similar insertion or snapping mechanism is provided for charging and/or reprogramming the BEM between usages. Alternatively to an insertion mechanism in the charging station, the BEM can have an additional telemetry coil for inductive charging or wireless control during infusion. A standard micro or regular USB connection may be utilized, and a water-resistant or waterproof standard packaging can be employed to protect the BEM.

Figure 5:
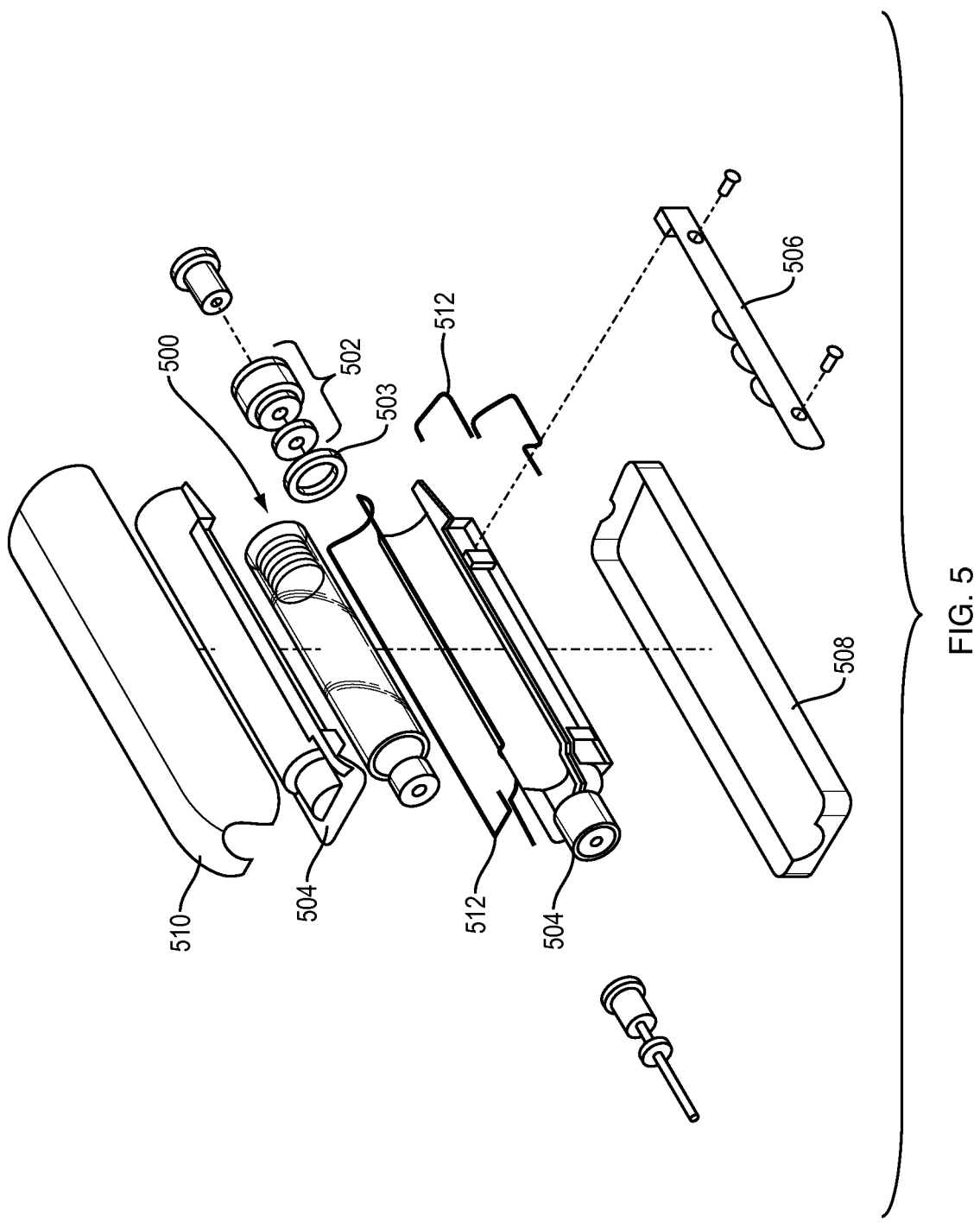
FIG. 5 is an exploded view of another piston pump device in accordance with various embodiments.

FIG. 5 illustrates another design of a high-pressure pump device. Here, the drug vial 500, pump assembly 502 (including an electrode structure and absorbent material), and O-ring 503 are enclosed in a separate, two-part housing 504, and the electronics/battery module 506 is placed on the side of the enclosed vial 500. An outer case includes bottom and top portions 508, 510 that are closed around the pump housing 504, the electronics/battery module 506, and associated tubing 512.

Figure 6A:
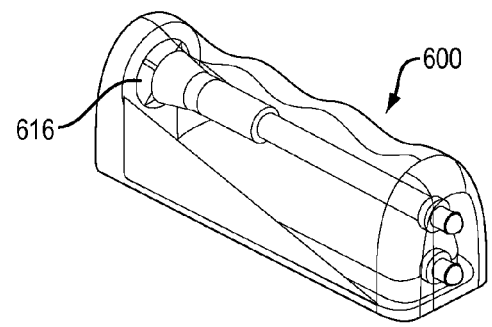
FIGS. 6A and 6B are isometric and exploded views, respectively, of a pump device with integrated lancet insertion mechanism in accordance with various embodiments.
Figure 6B:
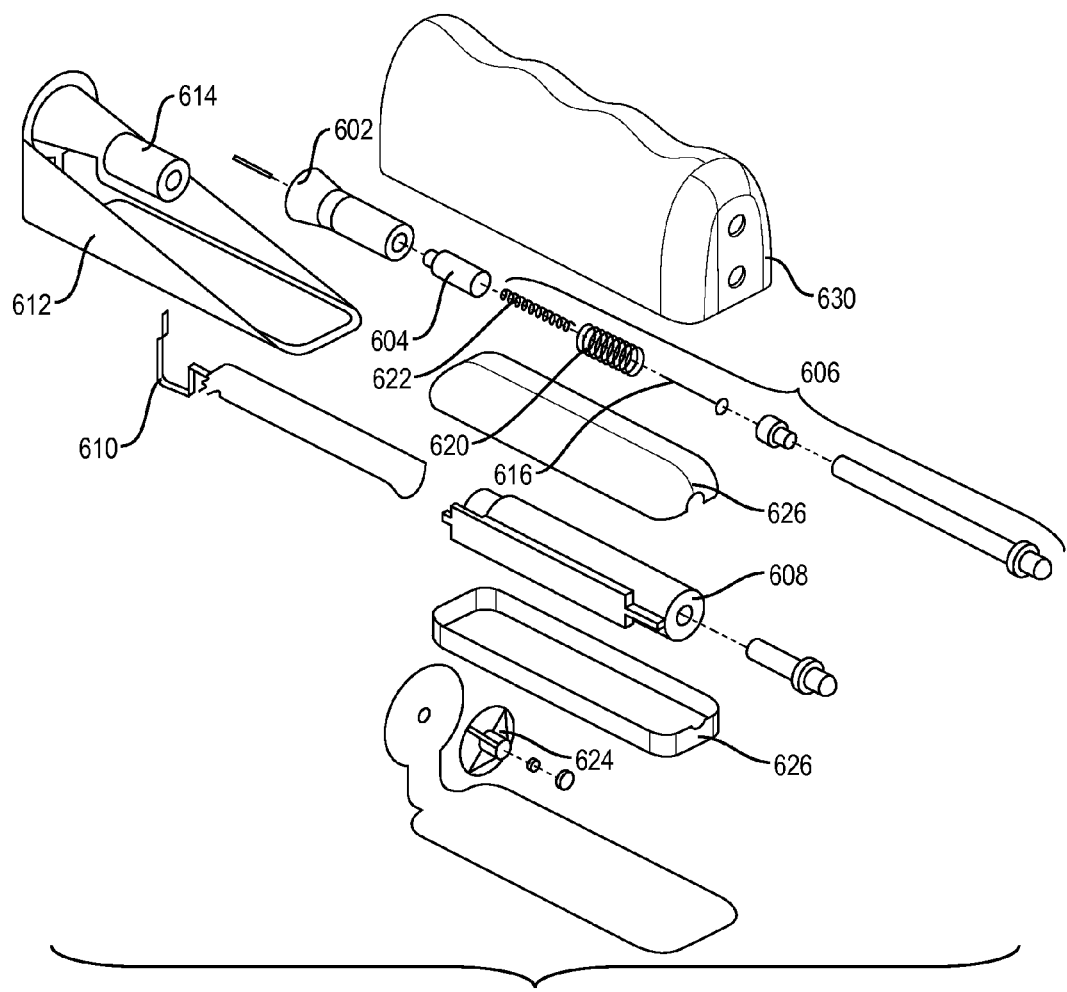

FIGS. 6A and 6B depict an exemplary piston pump device 600 with an integrated lancet-insertion assembly. The insertion assembly includes a serter housing 602, needle carrier 604, and needle/catheter double-spring insertion mechanism 606, and is disposed above a prefilled cartridge pump 608 (including the drug reservoir and electrolysis pump) and fluidically connected therewith via tubing 610. A carrier 612 provides a base for the cartridge pump 608, and a connector 614 for the insertion assembly. The serter housing 602 holds the needle 616 and a catheter 618 (e.g., made of Teflon) that connects thereto, as well as the two springs 620 (for insertion of the needle and catheter), 622 (for subsequent retraction of the needle), and connects to the catheter hub 624. The cartridge pump 608 may be contained in a pump casing 626, which, together with the insertion assembly, is enclosed in an outer device shell 630.

Figure 7B:
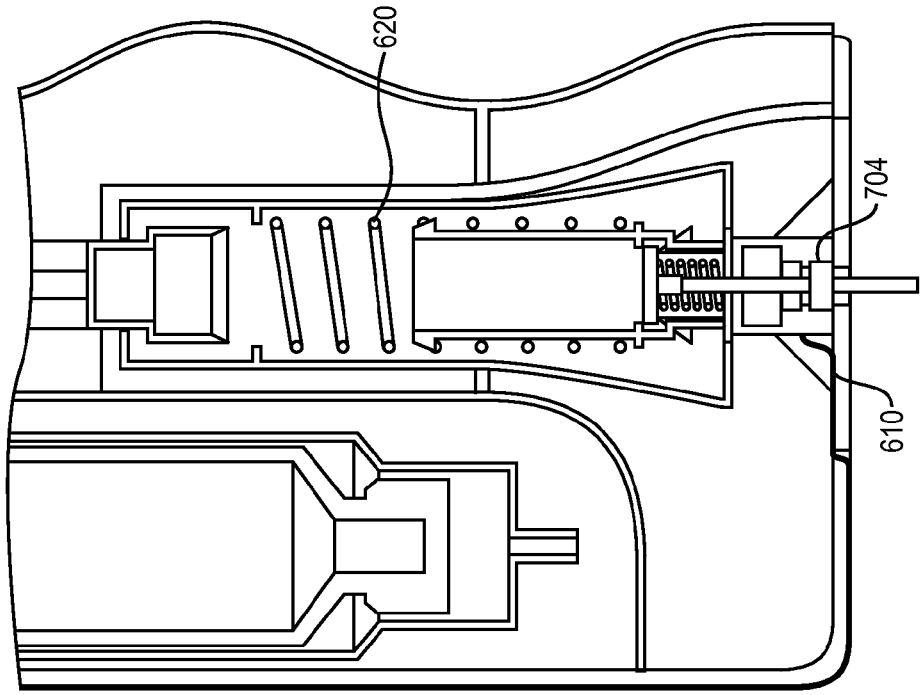
FIGS. 7A-7C are side views illustrating different stages of lancet insertion using the device of FIGS. 6A and 6B.
Figure 7A:
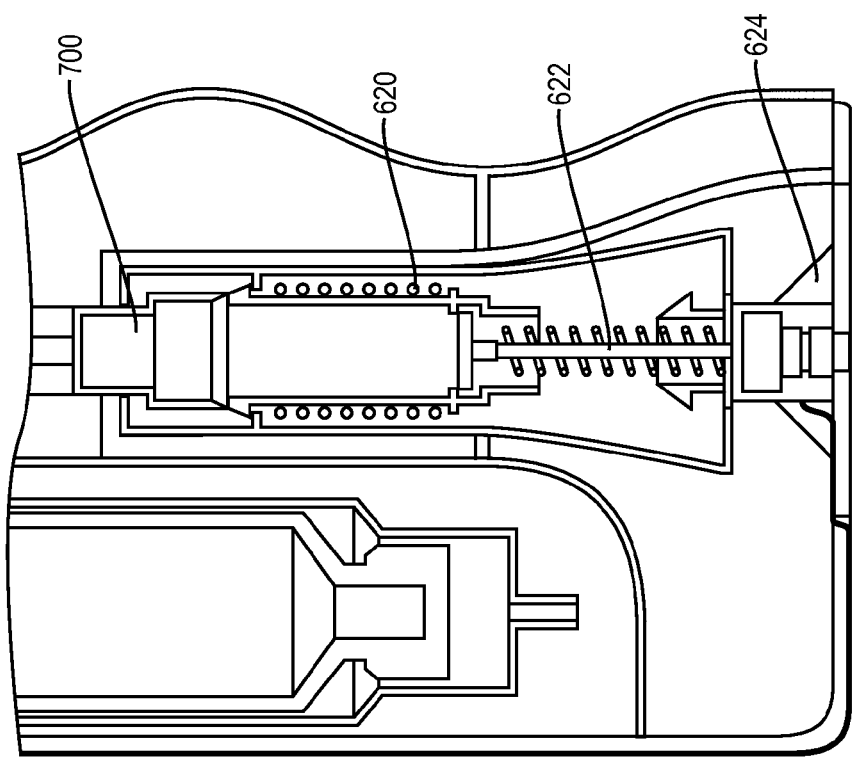
Figure 7C:
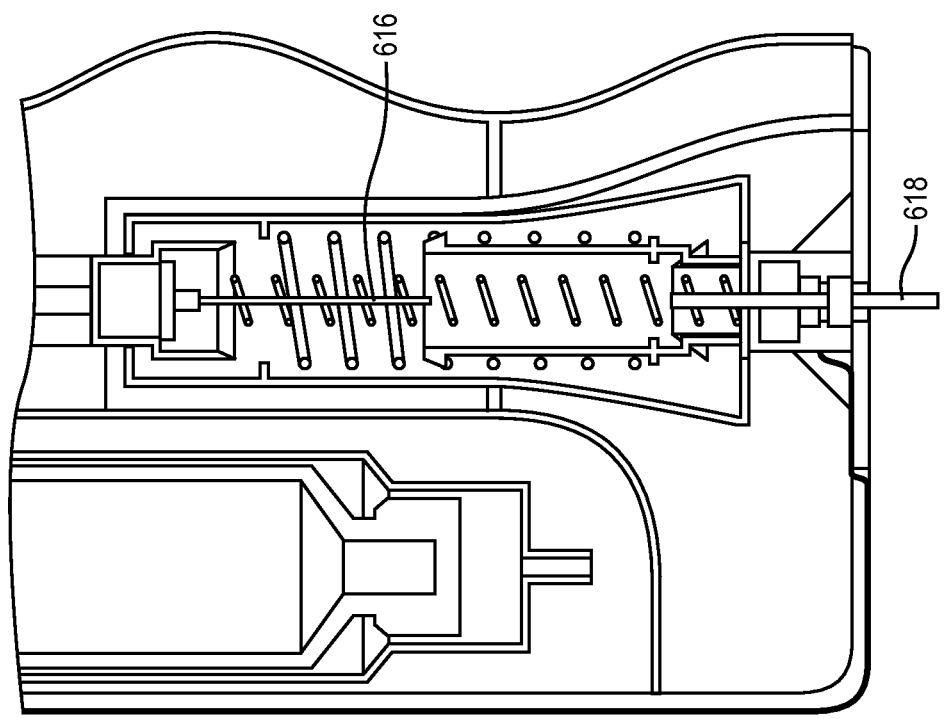

FIGS. 7A-7C illustrate the mechanism of inserting a catheter into the subcutaneous tissue. In the initial position, the needle 616 and catheter 618 are located above the catheter hub 624. By activation of a trigger button 700, the insertion spring 620, which is initially compressed, is released. This moves the needle 616, needle carrier 604 and catheter 618 (hereafter the "needle carrier assembly") downward, inserting the needle 616 with the catheter 618 through a self-sealing silicone plug 704, and into the subcutaneous tissue (FIG. 7B). The self-sealing silicone plug 704 has two septums (top and bottom layers), providing an open area between the two layers with which the outlet of the fluid tubing 610 fluidically communicates. During insertion, the needle carrier assembly is propelled downward by the spring 620, and is stopped when the front (i.e., downward-facing in the figure) face of the needle carrier 604 encounters the rear (upward-facing) face of the catheter hub 624. The catheter hub 624 may have angled sides, which act as latches, holding the retraction spring 706 (which is still compressed) in place. The retraction spring 622 is at least as stiff as, and typically stiffer than, the insertion spring 702; thus, when released, it can compress the insertion spring 702 and drive the needle carrier assembly back into its original position. When the user compresses the sides of the catheter hub 624 with thumb and forefinger, the retraction spring 622 is released. As a result, the needle 616 is extracted out of the tissue as the needle carrier assembly is driven back into the retracted position (FIG. 7C). When the needle is retracted, radial and axial compression on the silicone plug 704 causes the small puncture to close immediately, providing a tight seal for the fluid path in the infusion set. Following catheter insertion, the lancet insertion assembly and outer shell may be removed, leaving only the pump and infusion set on the skin. An alternative catheter insertion mechanism is described in U.S. Provisional Application No. 61/704,974.

Figure 8:
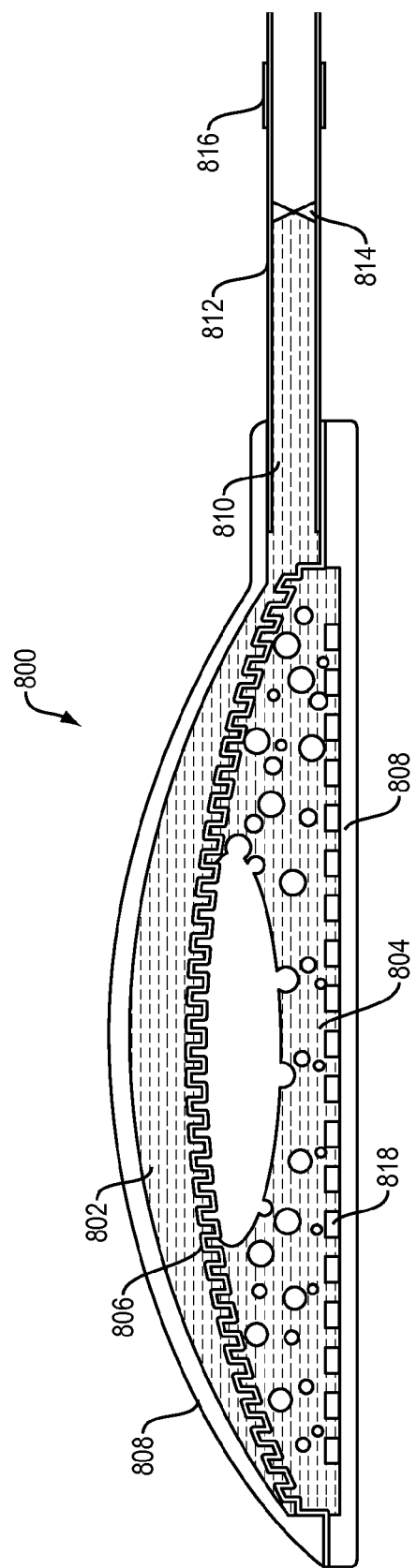
FIG. 8 is a schematic side view of a diaphragm pump device in accordance with various embodiments.

In diaphragm pumps 800, illustrated schematically in FIG. 8, the drug reservoir 802 and pump chamber 804 are stacked in a double-chamber configuration, in which the drug reservoir 802 is separated from the pump chamber 804 by a flexible diaphragm 806. Typically, the pump chamber 804 is formed between the bottom portion of the housing 808 (which may be attached to a skin patch) and the diaphragm 806; the drug reservoir 802 is disposed above the pump chamber 804, and is formed between the diaphragm 806 and a dome-shaped portion of the housing 808. Electrolysis gas developed in the pump chamber 804 exerts pressure on the diaphragm 806, which, as a result, expands, expelling liquid drug through an outlet 810 of the reservoir into a cannula 812 (or other exit member). The cannula 812 may be equipped with a check valve 814 and flow sensor 816. The control circuitry and battery (not shown) may be mounted on a circuit board integrated into the bottom portion of the housing 808. In some embodiments, the electrodes 818 are etched, printed, or otherwise deposited directly onto the circuit board for cost-savings and ease of manufacturing.

To facilitate accurate basal and/or bolus drug deliveries with drug pump devices such as, e.g., those illustrated in FIGS. 2B and 8, various embodiments of the invention utilize a combination of (1) flow restriction downstream the reservoir in conjunction with high pump pressures, (2) pressure-relief mechanisms that speed up the pressure drop upon cessation of electrolysis, and (3) sensor-based feedback for electrolysis pump control. The following sections describe each of these features in more detail.

Flow Restrictors

Figure 9A:
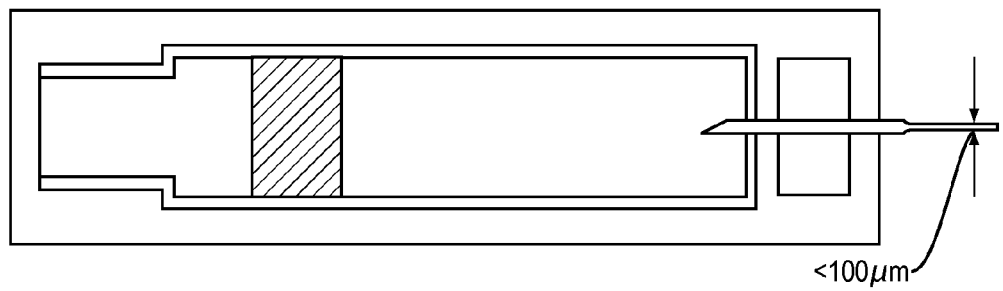
FIGS. 9A-9C are schematic side views of flow restrictors in accordance with various embodiments.
Figure 9B:
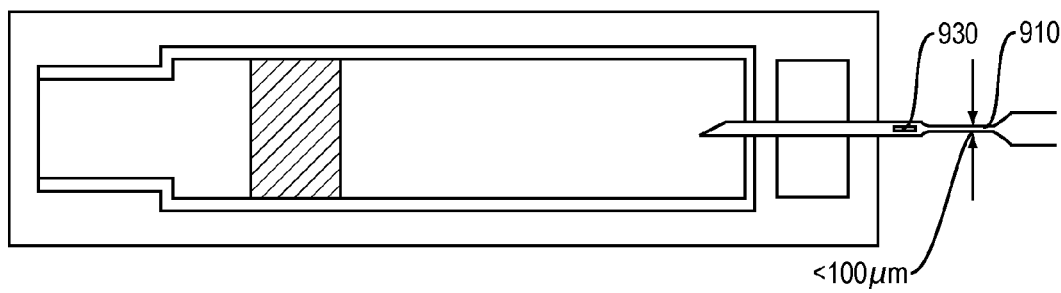
Figure 9C:
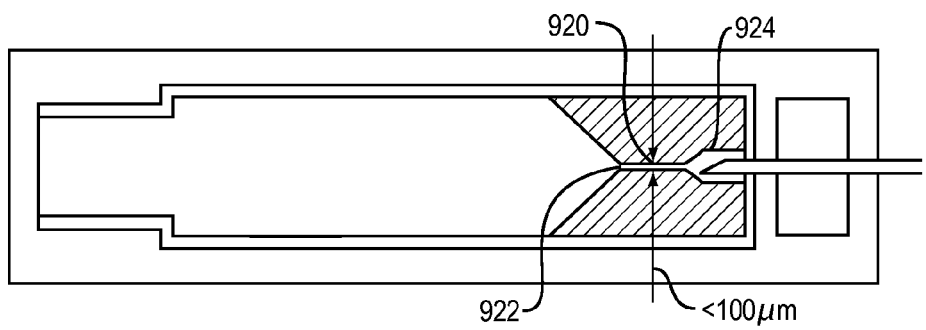

To stabilize the delivery flow rate despite variations in friction and/or other pump conditions, a flow restrictor may be utilized downstream the reservoir. In some embodiments, the exit member 108 itself serves as the flow restrictor. For example, the cannula or needle conducting fluid from the drug reservoir to the injection site, or a portion thereof, may have a small inner diameter, e.g., a diameter of less than 100 μm, less than 50 μm, or less than 25 μm; this embodiment is illustrated in FIG. 9A. Alternatively, a separate flow-restrictor element may be integrated with the exit member, as shown in FIG. 9B; this allows for flow restriction despite the use of conventional needles and cannulas, whose inner diameters are typically in the range from 100 μm to 500 μm. The flow restrictor may simply constitute a portion 910 in the fluid path having a small inner diameter, or may include a valve or similar structure that can variably limit the flow rate (such as an iris-like valve with controllable inner diameter). In yet another embodiment, shown in FIG. 9C, a flow restrictor 920 is connected between the reservoir outlet 922 and an adaptor 924 into which the exit member is fluidically coupled during use. The flow restrictor 920 and adaptor 924 may be formed inside the vial as an extension of and integrated with the inner wall of the vial; the space surrounding the restrictor and adaptor structures inside the vial may be filled, e.g., with an epoxy, for mechanical stability. In general, any component and arrangement in the fluid path between the reservoir and the injection site that deliberately increases the downstream flow resistance may serve as a flow restrictor in accordance herewith.

In certain embodiments, the flow restrictor is implemented by a micromachined microchannel device. A well-defined microchannel can be manufactured by either a surface or a bulk micromachining technique, as are well known to persons of skill in the art. The depth, width, and length of the microchannel can be machined with high accuracy, and the tolerance can be controlled down to nanometers. Further, with a visual inspection using an industrial, standard, fully-automated microscopic inspection system, the fabricated microchannel flow restrictor can be fully examined without causing a significant increase in manufacturing cost. The micromachining process is also very suitable for mass production. Compared to micro-capillary flow restrictors made by a traditional high-accuracy protrusion process requiring 100% manual flow-rate/flow-resistance calibration, screening, and quality control, micromachined microchannel devices can provide cost savings in both manufacturing and quality inspection.

The flow restrictor is preferably dimensioned so that it dominates the overall flow resistance of the drug pump device. As a consequence, fluctuations in the flow resistance imparted by other parts have a significantly reduced effect on the flow rate. For the purpose of illustration, assume, for example, that the flow resistance of a conventional piston pump device is due, in equal parts, to the exit member and vial/piston friction. A sudden drop in the friction between vial and piston to half of its previous value then causes the overall flow resistance to change by 25%. If the flow resistance of the exit member is increased by a factor of 10, however, the same drop in friction results in a flow-resistance change of only about 4.5%. It can thus be seen that a deliberately introduced high flow resistance reduces the relative impact of any fluctuations in flow resistance of other device components, thereby smoothing and stabilizing the flow rate. Of course, without any commensurate changes in the driving pressure, an increased flow resistance would result in lower flow rates. Since the desirable flow rates in drug pump devices are usually dictated by medical considerations, devices in accordance with high-flow-resistance embodiments are generally driven at high driving pressures. The case and the connection of the pump are, accordingly, designed to withstand much higher internal pressure without causing any leakage.

Figure 10A:
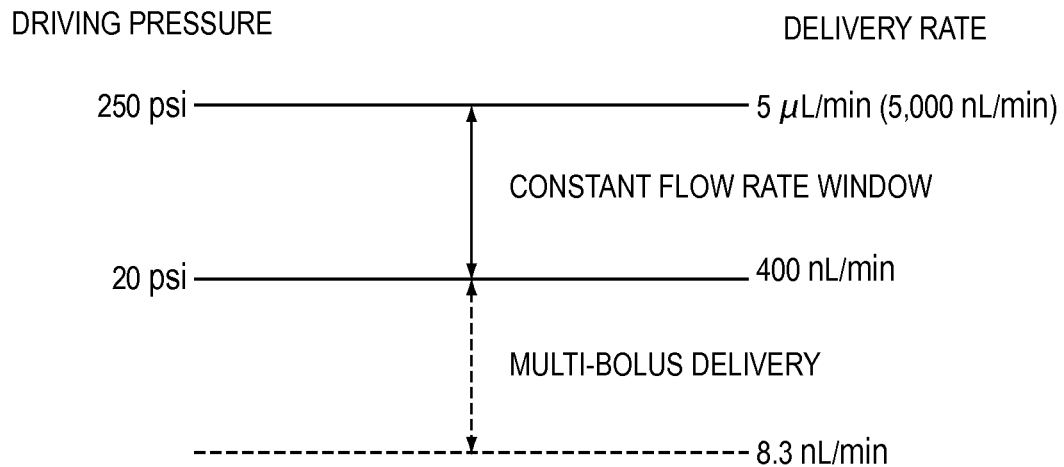
FIGS. 10A and 10B are diagrams illustrating high-flow-resistance and low-flow-resistance operational regimes of drug pump devices in accordance with various embodiments.
Figure 10B:
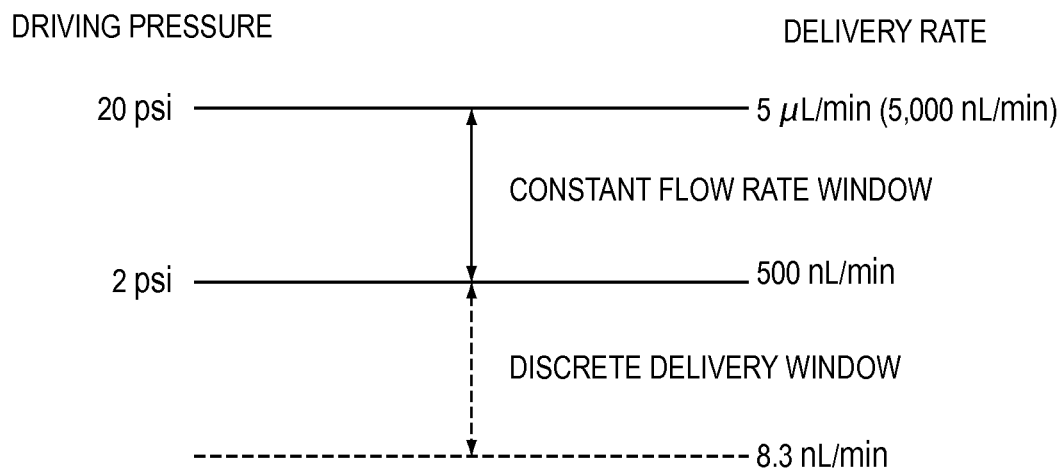

FIG. 10A depicts a typical flow regime for insulin delivery, as achieved using a high-resistance outlet (e.g., an exit member having an inner diameter of less than 100 μm). The desirable basal flow rate is in the range from about 8.3 nl/min to about 5 μl/min. By carefully calibrating the flow resistance of the outlet tube by properly selecting its dimensions (i.e., length and inner diameter), a flow rate of 400 nl/min under a driving pressure of 20 psi can be obtained. Further, due to the fixed flow resistance of the outlet, the flow rate increases linearly with the driving pressure. Thus, by increasing the driving pressure by a factor of 12.5 to 250 psi, the delivery flow rate can also be increased by a factor of 12.5 times to 5000 nl/min. Within this delivery window (400-5000 nl/min), the delivery is truly continuous (not discrete like with commercial step-motor pumps). Lower flow rates (between 8.3 and 400 nl/min) can be achieved via multi-bolus deliveries, as further explained below. The same flow rates as shown in FIG. 10A can also be accomplished at lower pressures if a correspondingly lower resistance is used at the outlet (e.g., if the exit member has an inner diameter substantially greater than 100 μm); FIG. 10B shows, for example, an embodiment where flow rates between 400 nl/min and 5 μl/min are generated by driving pressures ranging from 2 psi to 20 psi. In general, however, the lower the pressure/flow-resistance combination, the stronger is the effect of any fluctuations in the resistance imparted by the piston/vial subsystem. To ensure a high flow-rate stability, is therefore desirable to work at higher flow resistances and pressures, provided, of course, that the pump device is able to withstand such pressures without breaking or leaking.

For different drug therapies, different flow rate regimes than those shown in FIGS. 10A and 10B may be required. The flow resistance and/or driving pressures can be adjusted straightforwardly to achieve these different flow rates while stabilizing the flow rate in accordance herewith. Further, for different vial and pump systems, different pressure and flow-resistance levels may be preferable for any given flow rate, and can be determined by a person of skill in the art without undue experimentation.

The relation between driving pressure and delivery rate is given by:

$$P = Q \times R$$

where P is the driving pressure (less any back pressure at the injection site, which is, however, generally negligible), Q is the delivery rate, and R is the flow resistance of the device. In embodiments with a high-resistance flow restrictor downstream the reservoir, as contemplated herein, the contribution of the piston and vial (and any lower-resistance portions of the fluid path downstream the reservoir) is negligible, and R becomes, essentially, the flow resistance of the flow restrictor. For a tubular flow restrictor with length/and inner diameter D, the flow resistance can be expressed by the following relation:

$$R = \frac{128\,\mu l}{\pi D^4} \equiv \mu f_r \propto \frac{1}{D^4}$$

where $\mu$ is the dynamic viscosity of the fluid and $$f_r = \frac{128 l}{\pi D^4}$$

is the flow resistance factor, which is defined for the purposes hereof to characterize the flow resistance provided by the flow restrictor independently of the fluid.

In various embodiments, the flow resistance is at least 1 psi/($\mu$l/min), at least 2 psi/($\mu$l/min), at least 4 psi/($\mu$l/min), or at least 10 psi/($\mu$l/min), and in certain embodiments it is as high as, e.g., 50 psi/($\mu$/min). For ordinary drug-fluid viscosities, which are in the range from about 1 cP to about 35 cP (where 1 cP=1 mPa·s is the approximate viscosity of water at room temperature), such high flow resistances can be achieved using flow restrictors of 1-15 cm in length with diameters of less than 100 $\mu$m, preferably less than 50 $\mu$m, resulting in flow resistance factors in excess of $10^6 4 11$ and as high as $2.10^9$ $\mu$l. For example, a flow restrictor that is 10 cm in length and has a diameter of 50 $\mu$m results in a flow resistance factor of about $6.5.10^8/\mu$l.

Pressure-Relief Mechanisms

To facilitate accurate bolus deliveries, it is important for the pump device to be able to shut down drug flow as fast as possible. However, while electrolysis can be interrupted almost instantaneously, the built-up electrolysis gas pressure in the pump chamber falls off over much longer time periods as the gas constituents (e.g., hydrogen and oxygen) gradually recombine into liquid electrolyte (e.g., water). It is, therefore, desirable to provide an efficient pressure-relief mechanism that helps reduce the driving pressure, and hence shut down drug flow, more rapidly. In preferred embodiments, the pressure can be reduced to substantially zero within 1-2 min or less; excessively rapid pressure relief, however, can cause safety concerns. Suitable mechanisms relieve pressure reproducibly, safely, and preferably controllably to enable reliable bolus delivery.

In general, any equipment or process that can physically, chemically, mechanically, electrically, electrochemically, or thermally decrease pressure by recombining electrolysis gases, removing gases from the pump chamber, or changing the format of the gases can be used for pressure relief. Further, with respect to their timing and duration, pressure-relief mechanisms generally fall into two categories. Mechanisms of the first type cause continuous recombination and/or release of electrolysis gas from the pump chamber, and work against the electrolysis pump during periods of active pump operation, i.e., when power is supplied to the electrolysis electrodes to produce electrolysis gas. In order to achieve a desired pump pressure in this case, the rate of electrolysis, and thus the electrolysis current, needs to be larger than in the absence of a pressure-relief mechanism. Once the electrolysis ceases, the mechanism operates to quickly reduce the amount of gas in the pump chamber; in other words, it accelerates the pressure drop upon interruption of gas generation. Mechanisms of the second type are actively triggered, and either operate for a duration that is inherent in the mechanism, or until they are interrupted by a control mechanism. Many such active pressure-relief mechanisms can be controlled so as to only partially relieve pressure in the pump chamber, rather than causing the pressure to drop to zero. For example, they may be operated to achieve a desired end pressure selected within a pressure continuum or among a number of discrete end-pressure levels. Variably controllable pressure-relief mechanism facilitate the delivery of bolus injections (e.g., of 10 $\mu$l each) in combination with a background basal rate (e.g., of 500 nl/min).

Figure 11A:
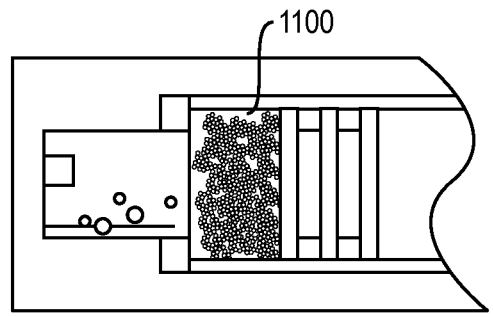
FIG. 11A is a schematic side view of a piston-pump electrolysis chamber with a catalytic pressure-relief mechanism in accordance with various embodiments.

An example of a continuously operating pressure-relief mechanism is the use of a recombination catalyst in the pump chamber, illustrated in FIG. 11A. Suitable catalyst materials for the recombination of the electrolysis gas include (without limitation) metals such as platinum, palladium, nickel, and iridium, and metal alloys such as nickel-cadmium, all of which decrease the activation energy for the formation of liquid water from gaseous hydrogen and oxygen. When the power to the electrolysis electrodes is turned off such that the recombination of hydrogen and oxygen to water is not off-set or surpassed by the reverse reaction, this phase change from gas-phase hydrogen and oxygen to liquid-phase water is accompanied by a significant decrease in volume—a shrinkage by about a factor of a thousand—and a corresponding large drop in the pump pressure. Catalytic materials can increase the rate of recombination by about an order of magnitude or more, compared with the baseline rate of recombination that takes place in the absence of any catalyst or other accelerating mechanism.

Nano-catalytic materials, such as nano-porous materials, nanowires, and nanoparticles offer significantly improved performance over normally-scaled catalysts. With the high surface-to-volume ratio of nano-structures, recombination rates in excess of two to three orders of magnitude (compared with the baseline rate) can be obtained. Examples of suitable nanomaterials include (but are not limited to) platinum black, platinum nanowires or nanoparticles, palladium nanowires or nanoparticles, and iridium nanowires or nanoparticles. As shown in FIG. 11A, these nanoparticles 1100 can simply be disposed within the electrolysis chamber during the manufacturing and assembly process, and can function there as is, constantly recombining hydrogen and oxygen. To inject a bolus of drug, electrical power is applied to produce gas at a rate higher than the recombination rate until the desired bolus volume is reached, at which time the power is turned off and the nanoparticles recombine the gases quickly to relieve the pressure and stop drug delivery.

Figure 11B:
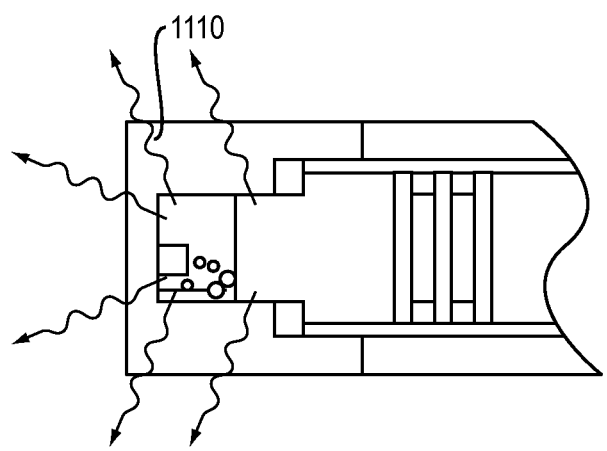
FIG. 11B is a schematic side view of a piston-pump electrolysis chamber with a semi-permeable housing in accordance with various embodiments.

Pressure relief based on continuous removal of the electrolysis gas from the pump chamber (at a rate lower than that at which gas is produced during active pumping periods) can be accomplished with a pump-chamber casing that is permeable to gas, but impermeable to liquid, as shown in FIG. 11B. Suitable materials include, for example, porous Teflon, porous sol-gel ceramics, and sintered porous metals such as stainless steel, aluminum, and titanium. The gas-permeable material need not form the entire portion of the casing around the pump chamber, but may be limited to a sub-portion in contact with the interior of the chamber that allows gas to escape from the chamber. In some embodiments, a tube inlet through which the chamber is initially filled with liquid electrolyte may be closed with a gas-permeable membrane, for example. In general, the rate of gas permeation through the gas-permeable casing portion or membrane can be pre-set by careful selection of the dimensions of the gas-permeable portion (e.g., its thickness and surface area) and the porosity of the material (e.g., the density and size of the pores). Via the permeability rate, the rate of pressure decrease after power shut-down can be controlled, allowing the device to be manufactured to achieve a particular desired bolus volume for a given electrolysis current.

Figure 11C:
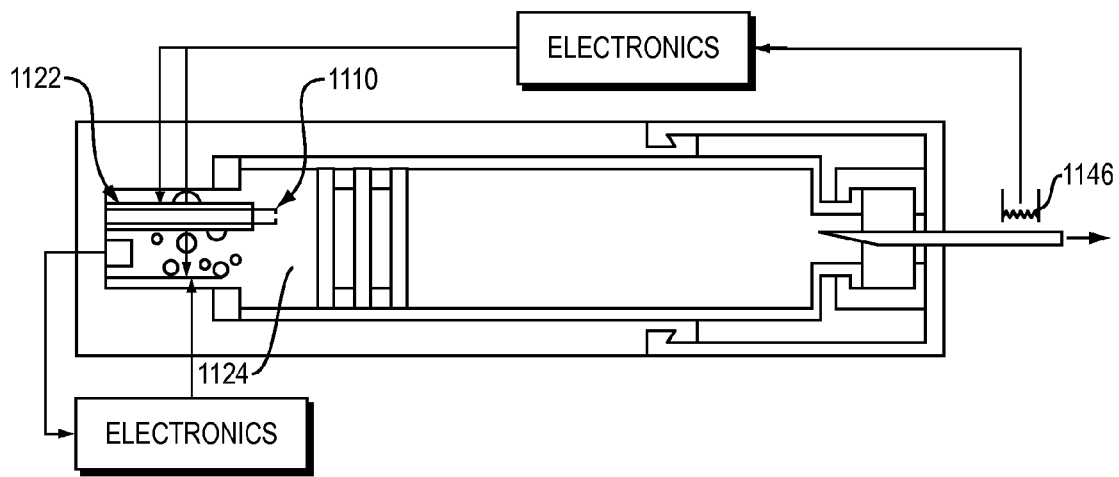
FIG. 11C is a schematic side view of a piston pump device with a spark-ignition recombination mechanism in accordance with various embodiments.

An example of a controllable pressure-relief mechanism is the creation of an electrical-discharge spark in the pump chamber that induces a rapid gas-recombination ignition process. Spark ignition can be achieved using any of a variety of suitable systems and processes, such as, e.g., capacitive-discharge ignition, inductive-discharge ignition, or transistor-discharge ignition. For example, as shown in FIG. 11C, a discharge arc can be created simply by application of a high voltage across a gap between two wires 1110 of a spark plug 1122 disposed in the chamber 1124. Like a chemical catalyst (as described above with respect to FIG. 11A), the spark decreases the activation energy between gas-phase hydrogen and oxygen to form liquid-phase water, causing the gases to recombine virtually instantaneously. The phase change from gas-phase hydrogen and oxygen to liquid-phase water can drastically decrease the volume of the substance (e.g., by a factor of about a thousand), and this sudden volume shrinkage provides the pressure relief. Recombination induced by spark ignition is very fast, usually resulting in nearly complete pressure relief (e.g., a drop down to 1% of the original pressure) within the microsecond to millisecond range.

Unlike spark ignition in a combustion engine, which causes gas expansion, spark ignition to induce gas recombination causes a volume decrease; consequently, there is no risk of explosion. Further, only minimal heat is produced during the process, likewise not presenting any safety risk. However, under certain conditions, the very fast pressure drop may induce a shock wave inside the pump chamber, potentially damaging certain delicate components installed in or around the chamber, such as a pressure sensor and circuitry. To avoid such problems, it may, therefore, be desirable to reduce the speed of spark-ignition recombination. A controllable and adjustable pressure drop is also advantageous for implementing drug-delivery protocols in which the pressure in between bolus deliveries is above zero, i.e., protocols that include a background basal rate. For bolus-basal deliveries, the driving pressure preferably decreases from a high bolus pressure to a low basal pressure in a controlled fashion rather than falling from the high pressure to zero and then going back to the low pressure; the former can reduce power consumption.

Figure 11D:
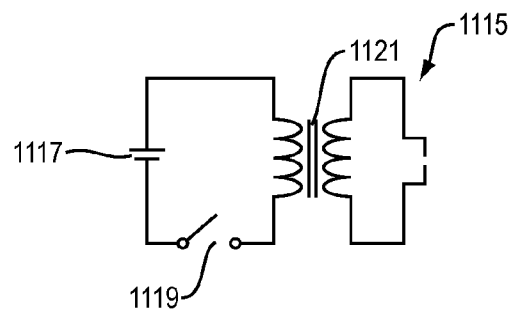
FIG. 11D is a circuit diagram for a spark ignition circuit that may be used in the embodiment of FIG. 11C.

One way to accomplish controlled, reduced-speed recombination is to shorten the ignition time of the spark. With a high-speed circuit 1115, as illustrated in FIG. 11D, the spark can be quickly turned on and off. The circuit 1115 is basically a spark-plug circuit that includes a DC source 1117, a momentary on/off switch 1119, and a high-voltage transformer 1121. In operation, the circuit 1115 operates in the manner of an automobile ignition circuit: current flows from the DC source 1117 through the windings of the primary coil of the transformer 1121, and when the current is disrupted by opening the switch 1119, the magnetic field of the primary transformer coil collapses rapidly. The secondary coil is engulfed by a powerful and changing magnetic field, which induces a current in the transformer coils—a very high-voltage current in the secondary coil because the number of windings therein is much larger than the number of windings in the primary coil. This voltage causes breakdown to occur, and current to flow in the form of a spark, across the spark gap. Thus, by shutting down the spark, recombination can be deliberately stopped before all the hydrogen and oxygen gases have recombined.

Figure 11E:
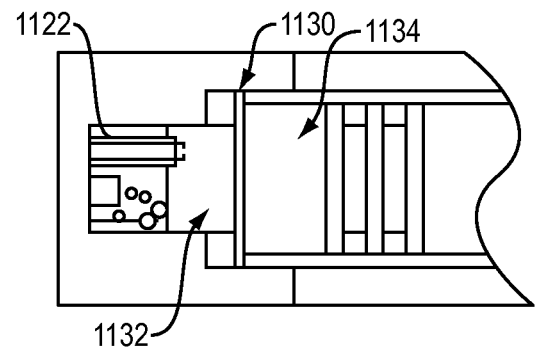
FIG. 11E is a schematic side view of a piston-pump electrolysis chamber as depicted in FIG. 11C that further includes a compartment separation in accordance with various embodiments.

Another way to slow down spark-ignition recombination is to use a separator 1130 to divide the interior of the pump chamber into two compartments 1132, 1134, as shown in FIG. 11E. The separator 1130 can be, for example, a valve, a membrane, a porous material, and/or a solid material with holes. Only gas in the compartment 1132 that includes the spark gap 1110 will recombine and reduce the compartment pressure to zero (or nearly zero); the gas mixture in the other compartment 1134, which is adjacent the piston, will gradually diffuse through the compartment separation (on times scales much longer than the duration of the spark) and replenish the first compartment 1132 until pressure equilibrium is reached. Via the volume ratio between the two compartments 1132, 1134, the end pressure can be set. For example, if the compartment 1132 that contains the spark gap takes up one fourth of the total pump chamber volume, the pressure will drop down to about one fourth of its original value. Repeated spark-ignition and pressure equilibration can, thus, be used to relieve the pressure incrementally (e.g., in the example, in factors of four). Of course, spark timing and compartment separation can also be used in combination in order to optimize recombination control.

An alternative approach to controllable pressure relief involves the use of an electrically resistive filament that is heated by application of an electrical current. This mechanism is similar to that used in incandescent lamps, where the filament acts as an electrical resistor and, upon application of sufficient power, the temperature of the filament rises to thousands of degrees Celsius. The thermal energy of the filament initiates recombination of the hydrogen and oxygen gases into water, and thereby lowers the pressure of the chamber. This mechanism provides a high degree of control, as the rate and duration of recombination can be readily adjusted via the magnitude and timing of the current applied to the filament.

Figure 11F:
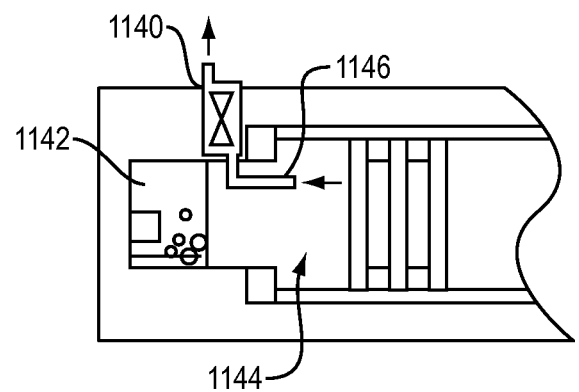
FIG. 11F is a schematic side view of a piston-pump electrolysis chamber with an active-valve pressure-relief mechanism in accordance with various embodiments.

Pressure relief can also be achieved by controllably releasing gas from the pump chamber using an active release valve, as shown in FIG. 11F. This valve 1140 can be normally closed (or have a small, controllable leakage rate that does not prevent pressure build-up in the chamber), and may be opened as needed to remove gas from the chamber 1144 and thereby relieve pressure. Typically, the valve is electromechanical or piezoelectric so that it can be controlled by the pump's control circuitry, which activates the valve as soon as the proper amount of drug has been pumped out (as indicated, for example, by readings from a flow sensor 1146 in the exit member). By closing the valve 1140 before all gas has escaped, the end pressure can be controlled—i.e., retained at an elevated level that does not expel drug but reduces the pressure buildup necessary for the next cycle of drug delivery. The valve 1140 may also facilitate control over the rate of gas release by providing different valve-opening sizes with associated different air-flow resistances. In some embodiments, the valve opening can be continuously adjusted by the pump controller, whereas in other embodiments, the valve provides a number of discrete size settings that the pump controller selects (or a single setting that is either open or closed). Suitable active pressure-relief valves include, but are not limited to, solenoid valves, diaphragm valves, ball valves, and duckbill valves.

To avoid ejecting electrolyte during the pressure-relief stage, which might cause the pump to eventually run out of electrolyte so that electrolysis reactions can no longer occur, the electrolyte may be soaked into a highly absorbent material, such as, e.g., a hydrogel, cotton fiber, sponge, or super-absorbent polymer. The electrolyte will then stay inside the absorbent material, separate from the gas compartment formed in the remainder of the gas chamber. The valve may be integrated into a portion of the chamber wall adjacent the gas compartment, and/or may be connected to a tube that opens into the gas compartment, as shown in the figure.

Sensor-Based Feedback Control

Figure 12A:
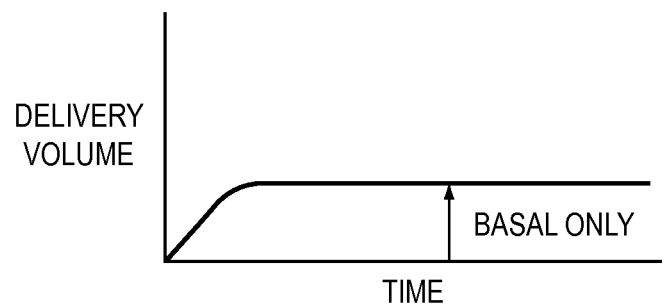
FIGS. 12A-12C are diagrams illustrating basal, bolus, and basal/bolus drug delivery modes in accordance with various embodiments.
Figure 12B:
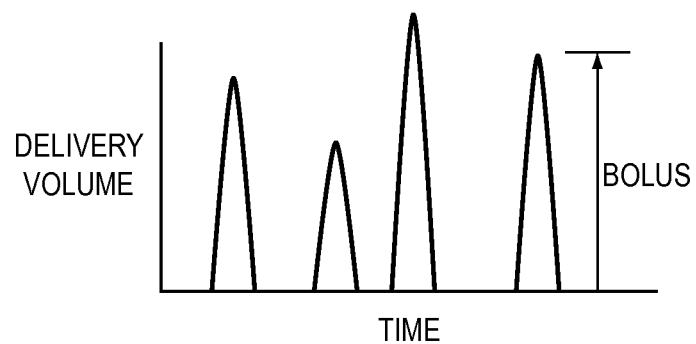
Figure 12C:
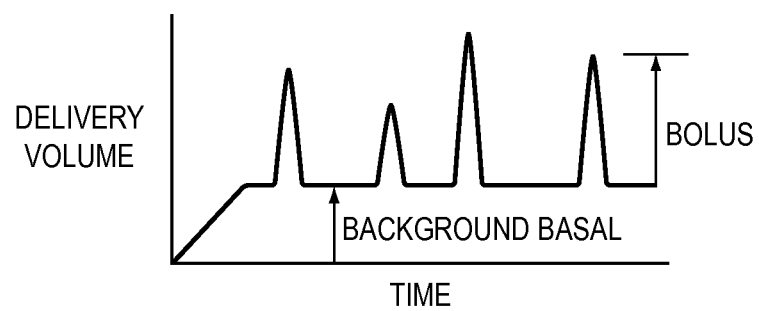

In various embodiments, drug delivery can be controlled via the electrolysis drive current to implement different delivery modes and protocols. A fully-functioned insulin pump, for example, enables three basic delivery modes for the treatment of different types of diabetes patients: (1) basal delivery at a constant rate of fluid injection, (2) bolus delivery (e.g., triggered manually by the patient or based on measured blood sugar levels, or at certain pre-programmed times throughout the day), and (3) background basal plus (multi-)bolus deliveries; FIGS. 12A-12C schematically illustrate delivery profiles corresponding to all three modes. A dinner pump, for instance, may administer a 150 µl dose of insulin immediately after dinner, and dispense another 350 µl at a basal rate over eight hours while the patient sleeps. Different diseases may require different delivery protocols, including complicated protocols that involve intermittent or continuous drug delivery at variable rates, with or without additional bolus injections. In general, a drug-delivery protocol may specify drug delivery times, durations, rates, and dosages, depending on the particular application. With reference to FIG. 1, the pump driver 110 may control delivery based on a selected preprogrammed delivery protocol (e.g., stored in system memory 120), or based on real-time commands received, e.g., via a telemetry module 124. A clinician may alter the pump programming in system memory 120 if the patient's condition changes.

High-accuracy pump control in accordance with a desired delivery mode or protocol typically utilizes sensor feedback. Different sensor types and feedback systems may be suitable for different modes. Feedback control schemes for basal, bolus, and combined basal/bolus delivery are described below. While these control schemes will be illustrated with reference to electrolytically driven piston pump devices (as described, e.g., with respect to FIG. 2A), it should be understood that many aspects and features of the control schemes are applicable to other types of drug pump devices as well.

Figure 13A:
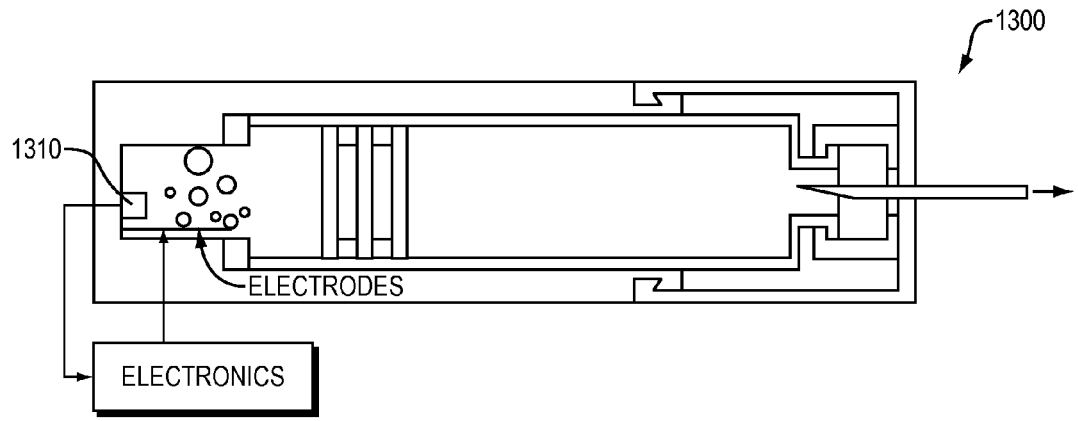
FIG. 13A is a schematic side view of a piston pump devices with pressure-based feedback for basal delivery in accordance with various embodiments.
Figure 13B:
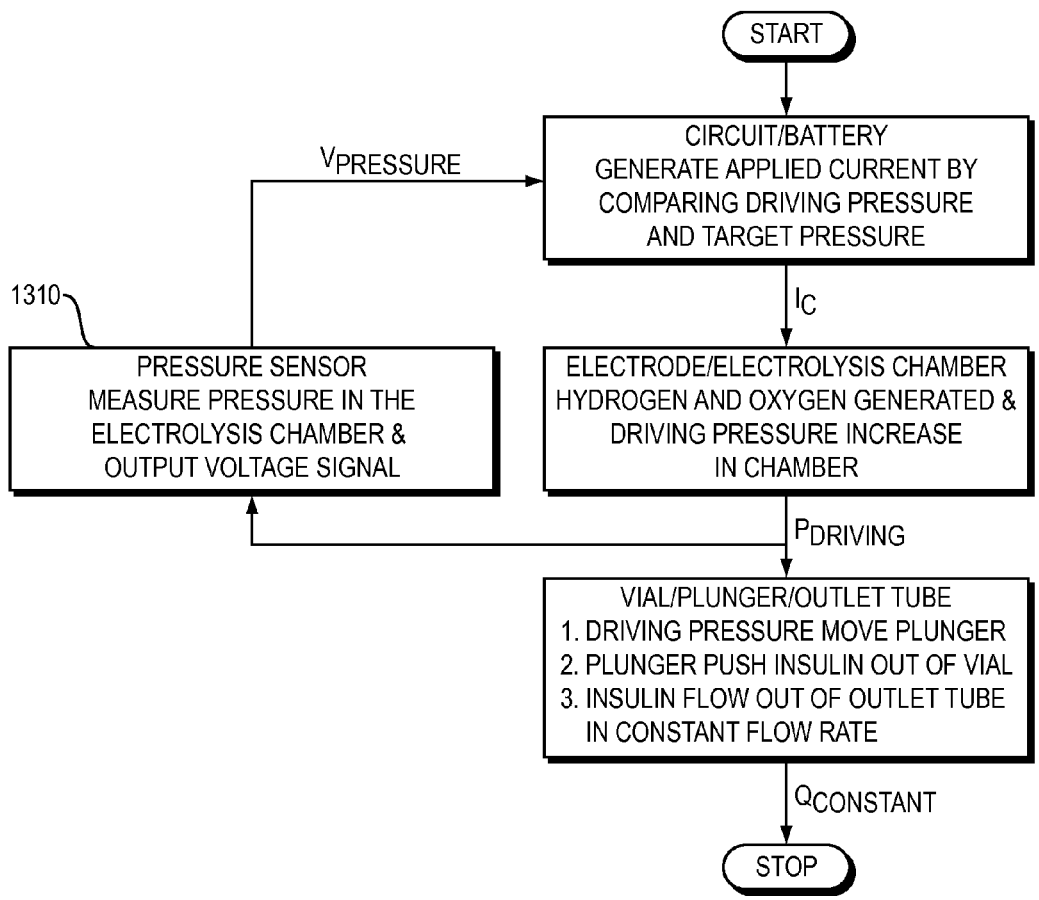
FIG. 13B is control-flow diagram for a pressure-based basal-delivery feedback loop in accordance with various embodiments.

FIGS. 13A and 13B illustrate, respectively, an exemplary piston pump device 1300 and an associated feedback loop for basal-rate delivery. To obtain a stable flow rate, the device 1300 is preferably equipped with a high-resistance flow restrictor at the outlet and operated at high driving pressures, as explained above. The driving pressure required to achieve a given target flow rate can be calculated based on the known flow resistance. The flow resistance, in turn, may be determined prior to device deployment—e.g., experimentally or by calculating it based on known outlet dimensions—and stored in memory (e.g., in memory of the system controller 112 or in separate system memory 120). Alternatively, the flow resistance may be determined by calibration before drug delivery begins, e.g., during the priming phase. If the flow resistance is known prior to device deployment, the target pressures for one or more target flow rates may likewise be calculated and stored in memory, e.g., in the form of a look-up table. Otherwise, the target pressure may be calculated by the system controller 112 at a later time based on input indicative of the target flow rate. In various embodiments, the pump is operated in a pressure regime in which the flow resistance is constant and the flow rate, consequently, is directly proportional to the driving pressure. However, the feedback loop illustrated in FIG. 13B is not contingent upon such a linear relationship, but can be employed whenever the relationship between flow rate and pressure is known.

To assure pump operation at the target pressure, the pump device 1300 may include a pressure sensor 1310 (e.g., an inexpensive, but accurate MEMS sensor as used in the automotive industry) that continuously monitors the driving pressure inside the pump chamber. Multiple pressure sensors may be used for increased accuracy and/or to detect sensor failure. As illustrated in FIG. 3B, the pressure sensor creates an output voltage (or other electric signal) indicative of the measured pressure that is fed back into the electronic circuitry. A signal conditioner may amplify and convert the analog voltage signal into a digital signal. This digital pressure signal is then provided to the system controller 112, which processes it in accordance with control code to compare the driving pressure with the target pressure. A differential output digital signal may be sent to the pump driver 110 to provide an analog control current for adjusting the power to the electrolysis pump accordingly.

In one embodiment, control logic implemented by the system controller 112 determines whether the measured pressure is within a specified margin (called the "bias") of the target pressure, and adjusts the electrolysis current according to the following steps: First, when the measured pressure is below the target pressure minus the bias value, the current is turned on. Then, when the measured pressure is within the range of the target pressure plus/minus the bias value, the current is reduced to a medium level. Finally, once the measured pressure is larger than the target pressure plus bias, the applied current is shut down. This process can be repeated continuously to adjust the rate of electrolysis so as to keep the pressure constant at the target pressure. Many other control methods may be used, including, without limitation, proportional-integral-derivative (PID) control, pulse-width modulation (PWM) control, artificial-neural-network (ANN) control, fuzzy-logic control, evolutionary computation control, model predictive control (MPC), and/or linear-quadratic-Gaussian control (LQG). The electrolysis current achieved by the various logic schemes may, in general, take any waveform; for example, it may be a square or triangular wave or be pulse-width-modulated.

Figure 14A:
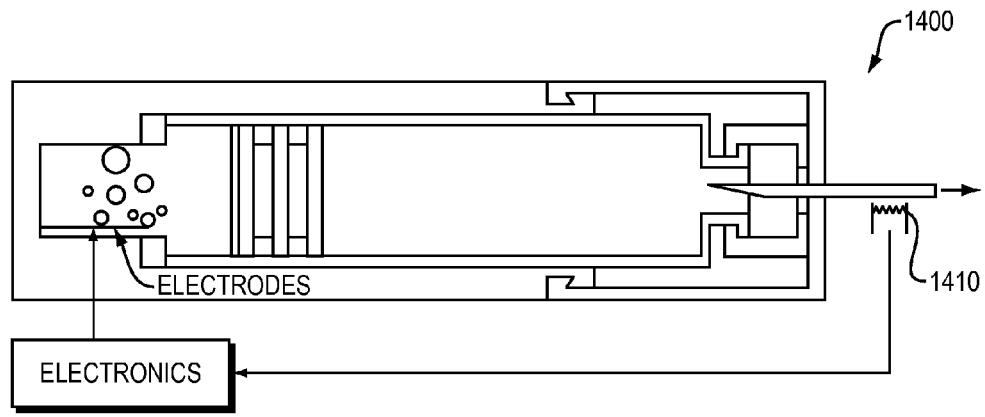
FIG. 14A is a schematic side view of a piston pump devices with flow-based feedback for basal delivery in accordance with various embodiments.
Figure 14B:
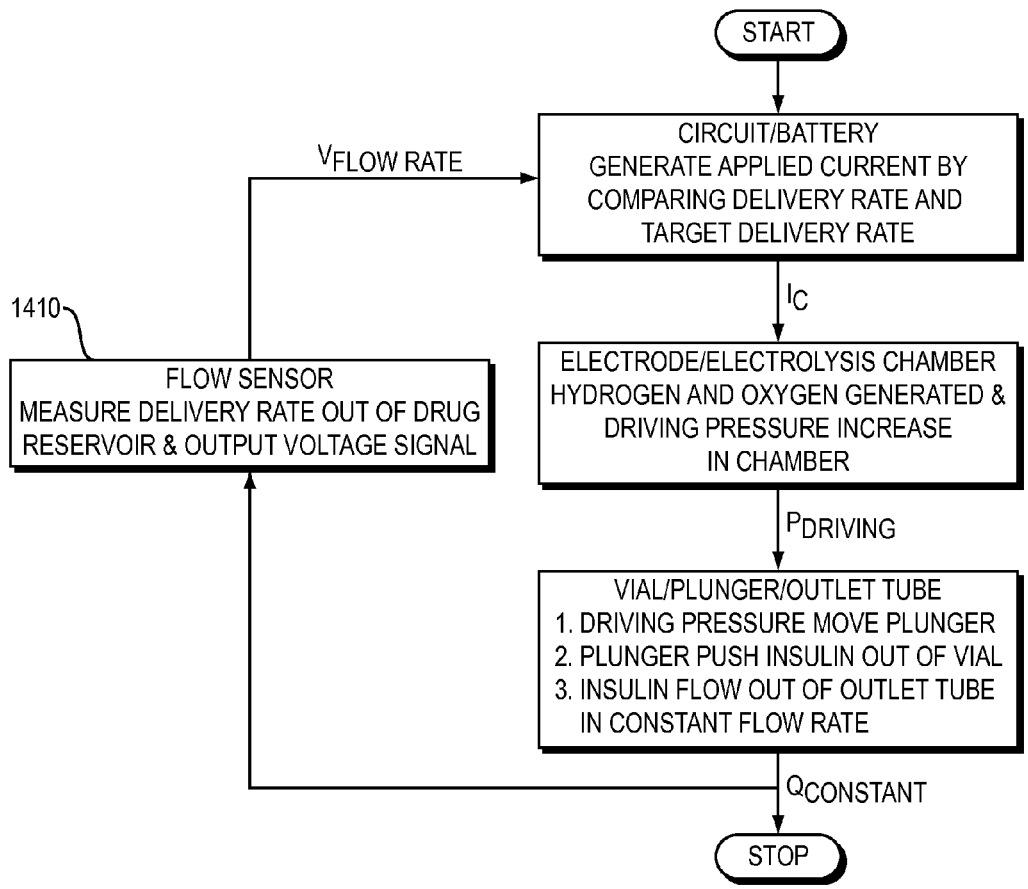
FIG. 14B is control-flow diagram for a flow-based basal-delivery feedback loop in accordance with various embodiments.

Using a high-pressure, sealed pump design in combination with feedback control of the electrolysis rate based on pressure measurements in the pump chamber, an accurate and constant flow rate for basal delivery can be achieved. As an alternative to pressure-based feedback, direct flow control can be implemented; this is illustrated in FIGS. 14A and 14B. The pump device 1400 includes, in this case, a flow sensor 1410 at the drug outlet or elsewhere in the exit member (downstream from the reservoir). This flow sensor monitors the actual delivery rate of drug flow out the exit member, and outputs a voltage signal that feeds back into the control system. As with the control method used for pressure feedback, the flow-rate voltage signal is compared with the target delivery rate, and the supply current to the electrodes is adjusted based on the difference between the target delivery rate and the measured delivery rate.

In yet another embodiment, the flow rate measurement itself is pressure-based: a pressure sensor (e.g., an inexpensive, yet accurate MEMS sensor as used in the automotive industry) connected to the drug outlet of the reservoir is used to measure the pressure, and the flow rate is obtained from the collected pressure data and the dimensions of the flow restrictor (or alternatively, the flow resistance as determined by calibration). The flow rate thus determined is then processed in the same manner as depicted in FIG. 14B, facilitating stable drug delivery at a constant rate. Using pressure sensors for flow-rate measurements can be preferable over direct flow-rate measurements with flow sensors because the latter are, in general, more expensive. In high-flow-resistance embodiments as described above, the pressure drop across the piston and drug reservoir is generally negligible, compared with that across the flow restrictor, such that pressure measurements in the pump chamber and the drug outlet, or anywhere in between (e.g., in the drug reservoir), yield approximately the same value.

Figure 15A:
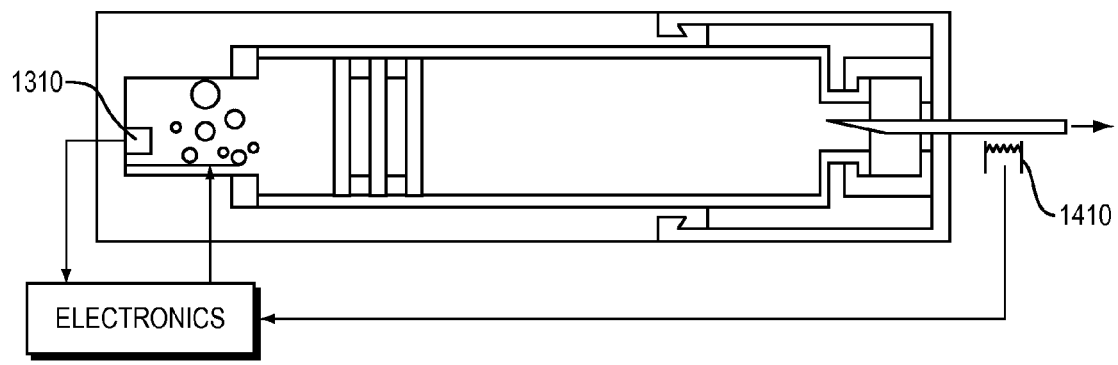
FIG. 15A is a schematic side view of a piston pump devices with dual-sensor feedback for basal delivery in accordance with various embodiments.
Figure 15B:
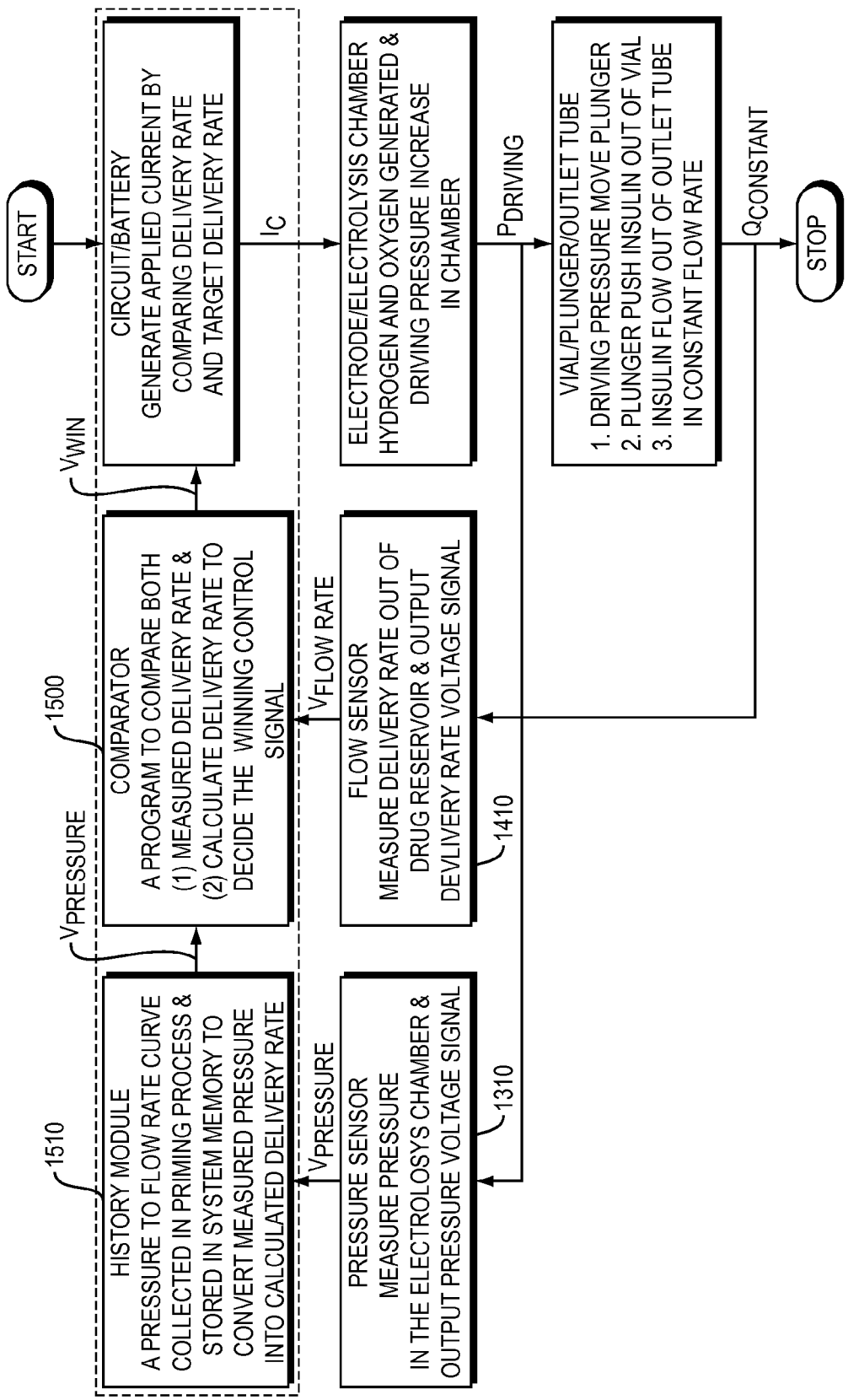
FIG. 15B is control-flow diagram for a basal-delivery dual-sensor feedback loop in accordance with various embodiments.

In applications demanding high delivery-rate accuracy and patient safety, a dual-sensor closed-loop feedback system can be used to provide extra control of the delivery rate. Advantageously, the use of two sensors allows for safe and controlled drug delivery even if one of the sensors experiences strong fluctuations or malfunctions. In dual-sensor feedback systems, both the pressure in the electrolysis chamber and the flow rate at or downstream from the reservoir outlet are measured and used as control signals, as illustrated in FIGS. 15A and 15B. A comparator 1500, which is typically implemented in programming, may select an action based on the signals from the sensors 1310, 1410. For example, the measured pressure value may be looked up against a pressure/flow-rate curve stored in a history module 1510 to find a corresponding calculated flow rate; the curve may be preloaded or obtained, e.g., during the priming stage. In some embodiments, any discrepancy between the measured and calculated flow rates beyond a tolerable margin is used as a trigger to initiate a safety protocol. This may involve shutting down the pump and issuing a warning signal, or restarting the pump to see whether renewed measurements are then in agreement.

In alternative embodiments, the comparator 1500 discriminates among or arbitrates between the two signals to adjust the electrolysis current based on one or the other, or both. For example, in one embodiment, if the measured flow rate agrees with the calculated flow rate within a set margin of error (e.g., the measured flow rate varies from the calculated flow rate by no more than 5%, 10%, or another fixed amount), then the measured flow rate is accepted and current control is based thereon (e.g., using the same kinds of control mechanisms as described above for pressure-based control, such as PID control, PWM control, etc.); otherwise, the calculated flow rate value is accepted and passed through as the correct flow-rate output value. This arbitration scheme is based on the assumption that the measured flow rate is either more accurate than the calculated flow rate, or so far off from the true value that it better be discarded entirely and substituted by the calculated flow rate. The scheme helps protect against untrue measurements of the flow rate, which may result, e.g., from air bubbles in the exit member or from sudden jerking motions, and can prevent premature activation or deactivation of electrolysis gas and pressure generation.

Alternatively or in addition, the control system may operate the pump based at least in part on recent pump operation via the history module 1510. Pump history may take the form of pressure and flow readings (as provided by the sensors 1310, 1410) measured continuously, over absolute time, or discretely at points in time when the electrodes are energized. Typically, a burst of readings will be stored following pump actuation as the pump operates; readings may or, more generally, may not be taken during quiescent periods.

The readings are stored in a shift register or circular buffer of the history module 1510; typically, newer readings replace older ones in FIFO order. The history module 1510 may enforce hysteretic operation of the pump, and the depth of the register or buffer determines the degree of hysteresis. For example, the recent history of the relationship between pressure and flow may be used to avoid jittery pump operation due to transient events, e.g., a momentary blockage of the exit member 108 by blood-borne debris. Rather than suddenly increasing pressure based on the instantaneous flow reading, the pressure is increased based on, for example, an average of the previous several flow readings stored in the history buffer. (The number of flow/pressure reading pairs used to determine a current pumping pressure depends on the application and is straightforwardly determined without undue experimentation. Furthermore, the number of reading pairs used may itself depend on the degree of departure from the previous flow readings, so that, for example, sudden spikes are smoothed out using more prior readings than smaller changes. In some embodiments, as few as three data samples are stored and averaged to predict the next.) Longer-term effects on flow, such as increasing blockage due to accumulation of biological material around the outlet port of the exit member 2410, are compensated for as the history readings revise over time the pressure/flow relationship (i.e., the amount of pressure necessary to achieve a target flow rate).

A dual-sensor feedback system may also utilize, instead of flow and pressure sensors, two pressure sensors. Typically, one pressure sensor is disposed within the pump chamber, and the other one is disposed at the outlet of the drug reservoir, i.e., downstream of the reservoir at a position where the reservoir-outlet pressure has not yet appreciably dropped. In embodiments with flow restrictors downstream of the reservoir, e.g., as shown in FIG. 9B, the second pressure sensor 930 is disposed in the fluid path between the drug reservoir and the flow restrictor 910. In embodiments that do not have a discrete component downstream of the reservoir and which dominates flow resistance (e.g., where the entire exit member, or a substantial portion thereof, functions as the flow restrictor), the second pressure sensor is generally placed as close to the reservoir as possible. When the flow resistance in the reservoir is high, the pressure drop across the drug vial is usually negligible. Thus, the pressure readings from both pressure sensors should be the same or nearly the same. In some embodiments, therefore, any appreciable difference between the two pressure readings (e.g., a relative difference exceeding 5% or 10% of the higher value, or some other predetermined difference) is taken as an indication of an error condition, and used to trigger pump shutdown or another suitable safety protocol.

Alternatively, the two pressure measurements upstream and downstream of the drug reservoir can be used to characterize the pressure drop across the reservoir as a function, e.g., of driving pressure. For example, for piston-pump devices with pre-filled drug vials, stiction/friction profiles can be measured and recorded prior to employment of the devices in patients. Different types of vials from different manufacturers can vary greatly in their quality and the friction generated between the interior vial wall and the piston, e.g., depending on whether or not the interior surface is coated with a friction-reducing layer. In some vials, even after the initial stiction forces are overcome, fluctuations in friction may cause piston movement to stop abruptly and, as the drive pressure is increased to resume drug delivery, start abruptly, entailing a risk of overdose to the patient. Rather than requiring and relying on low-friction vials and/or accurate a-priori knowledge of the effects of friction, drug pump devices with two pressure sensors in accordance herewith can calibrate friction and pressure drop across the drug reservoir for individual vials (and/or types of vials) to determine a suitable pump drive pressure and/or adjust for the now-known variations in pressure drop during drug delivery. A suitable drive pressure may be determined, e.g., by measuring the pressure drop and variations therein over a period of time for different drive pressures, and establishing a threshold pressure above which the pressure drop and, consequently, the flow rate at the outlet is sufficiently stable. Alternatively or additionally, pressure readings of the two sensors can be used during drug delivery to compensate for any remaining fluctuations in the pressure drop across the reservoir so as to maintain a constant flow rate.

In certain drug pump devices, flow rates of up to 1 ml/min, or even more, are established. In this case, a single pressure sensor may be used to assure proper pump operation. Safety concerns such as kinking or occlusion of a fluid path, or rupture of the pump chamber, will be readily detectable via the pressure measurements, and can be used to trigger shutdown of the pump.

Closed-loop feedback for electrolysis control has, so far, been described with respect to a constant basal flow rate. As those of skill in the art will appreciate, however, the control systems described above can readily be applied to variable target flow rates as well. For example, measured pressure or flow-rate values can be compared against a time-variable target pressure or flow rate, and the electrolysis rate be adjusted, in the manner depicted in FIG. 13B, 14B, or 15C.

Figure 16A:
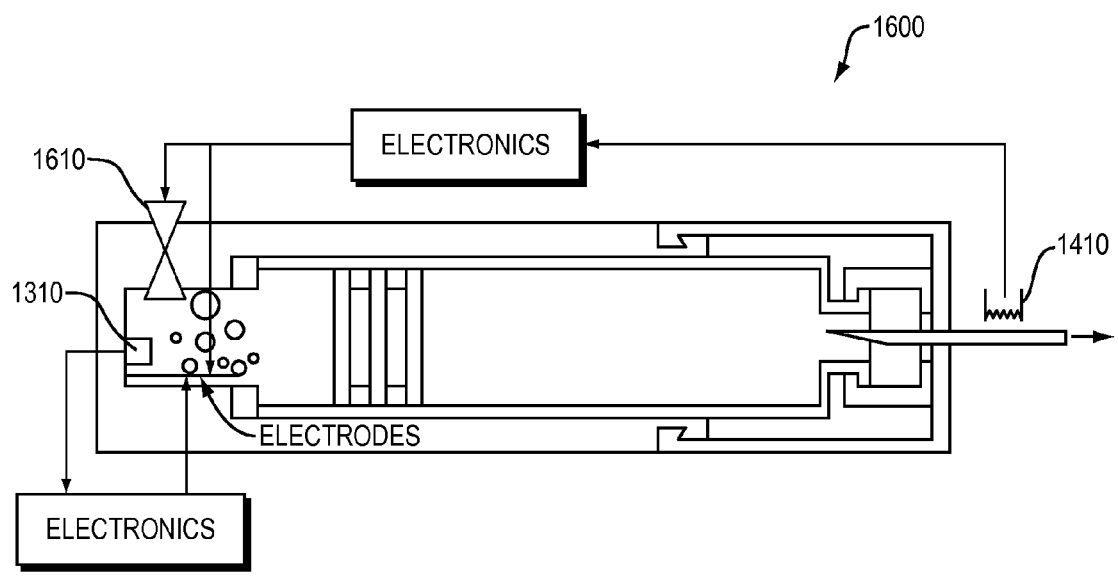
FIG. 16A is a schematic side view of a piston pump devices with dual-sensor feedback and a pressure-relief mechanism for basal/bolus delivery in accordance with various embodiments.
Figure 16B:
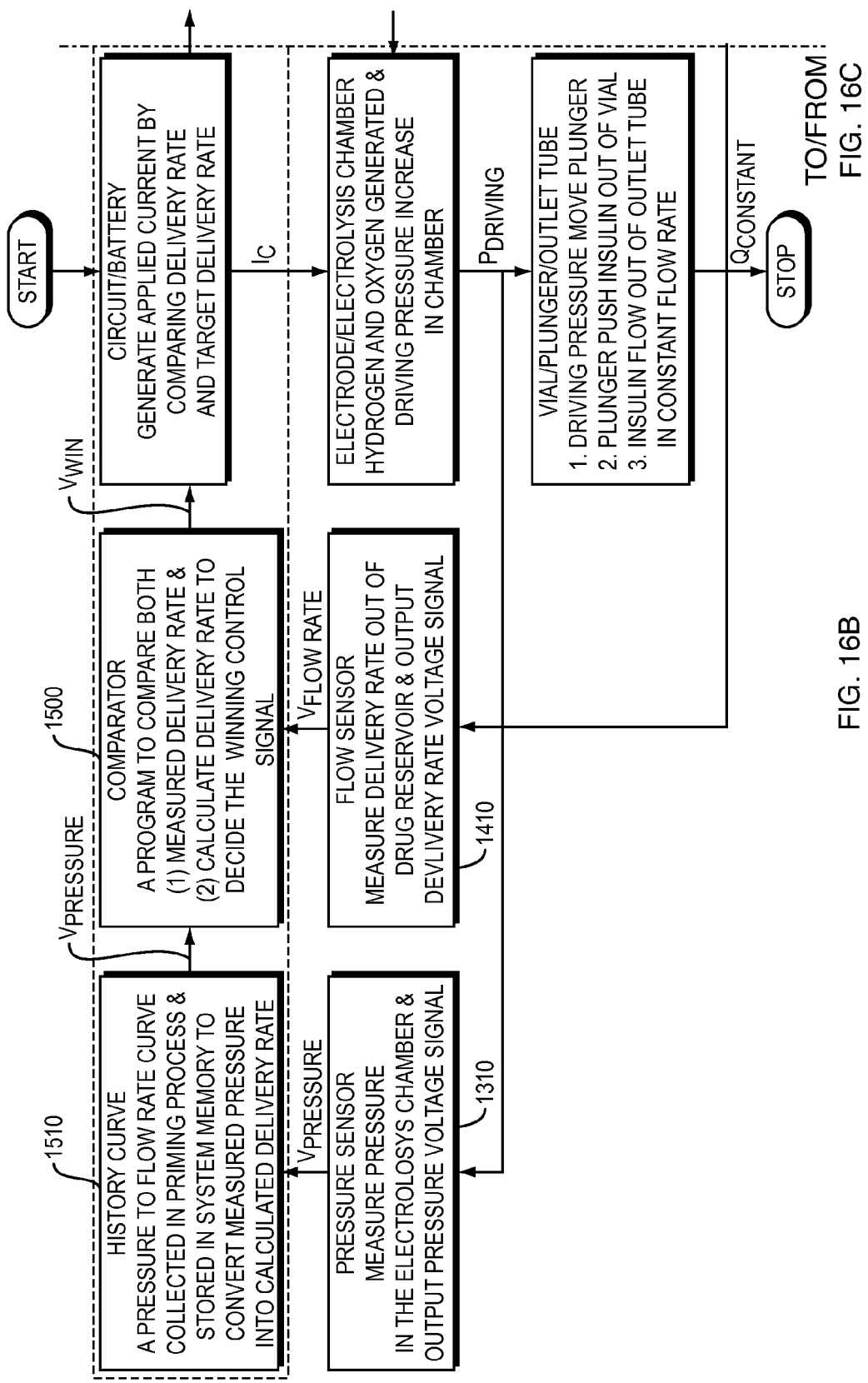
FIGS. 16B and 16C are control-flow diagrams for a basal/bolus-delivery dual-sensor feedback loop in accordance with various embodiments.
Figure 16C:
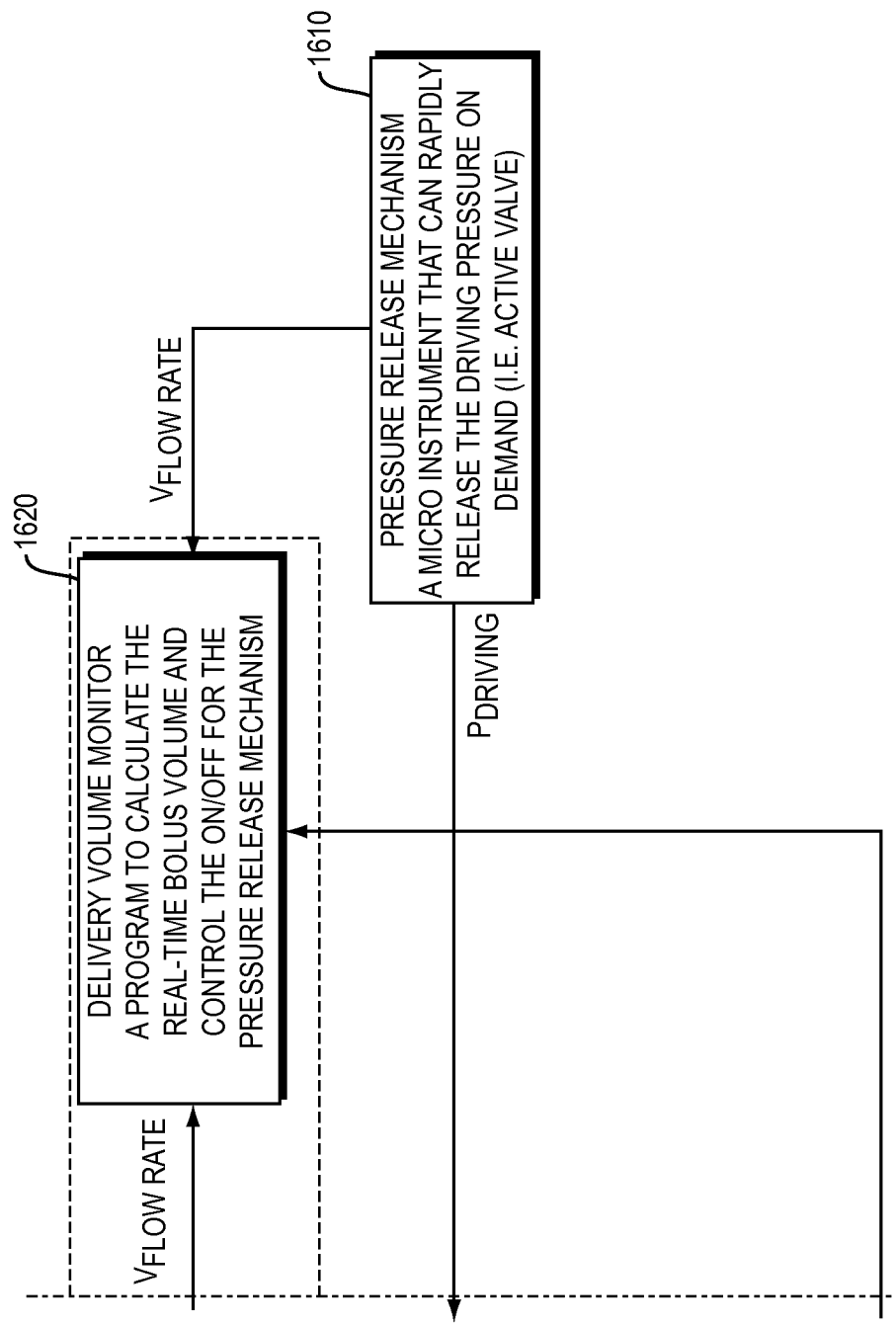

FIGS. 16A, 16B, and 16C illustrate an exemplary drug pump device 1600 and associated feedback system for accurate bolus delivery. The pump device 1600 includes, in addition to a flow sensor 1410 and related control circuitry, a pressure-relief mechanism 1610. While conceptually illustrated with a valve, the pressure-relief mechanism 1610 may be any of the mechanism described above (e.g., a recombination ignition spark, catalyst, etc.), or any other suitable mechanism that helps reduce pressure when the electrolysis pump has been deactivated. The flow sensor 1410 is used to monitor the real-time flow rate of drug delivered to the patient. A delivery-volume monitor 1620, which may be implemented in programming, integrates this real-time flow rate to calculate the delivered bolus volume in real time, and compares that volume against a target bolus dosage. When the delivered drug volume reaches the target bolus delivery volume, the system controller causes the pump driver to shut off the current to the electrolysis electrodes such that the pressure in the pump chamber begins to decrease. In pump embodiments that utilize an actively controllable (rather than continuously operating) pressure-relief mechanism, the system controller simultaneously triggers the mechanism. Thereafter, control of the electrolysis pump and/or the pressure-relief mechanism depends on the delivery mode.

Figure 17:
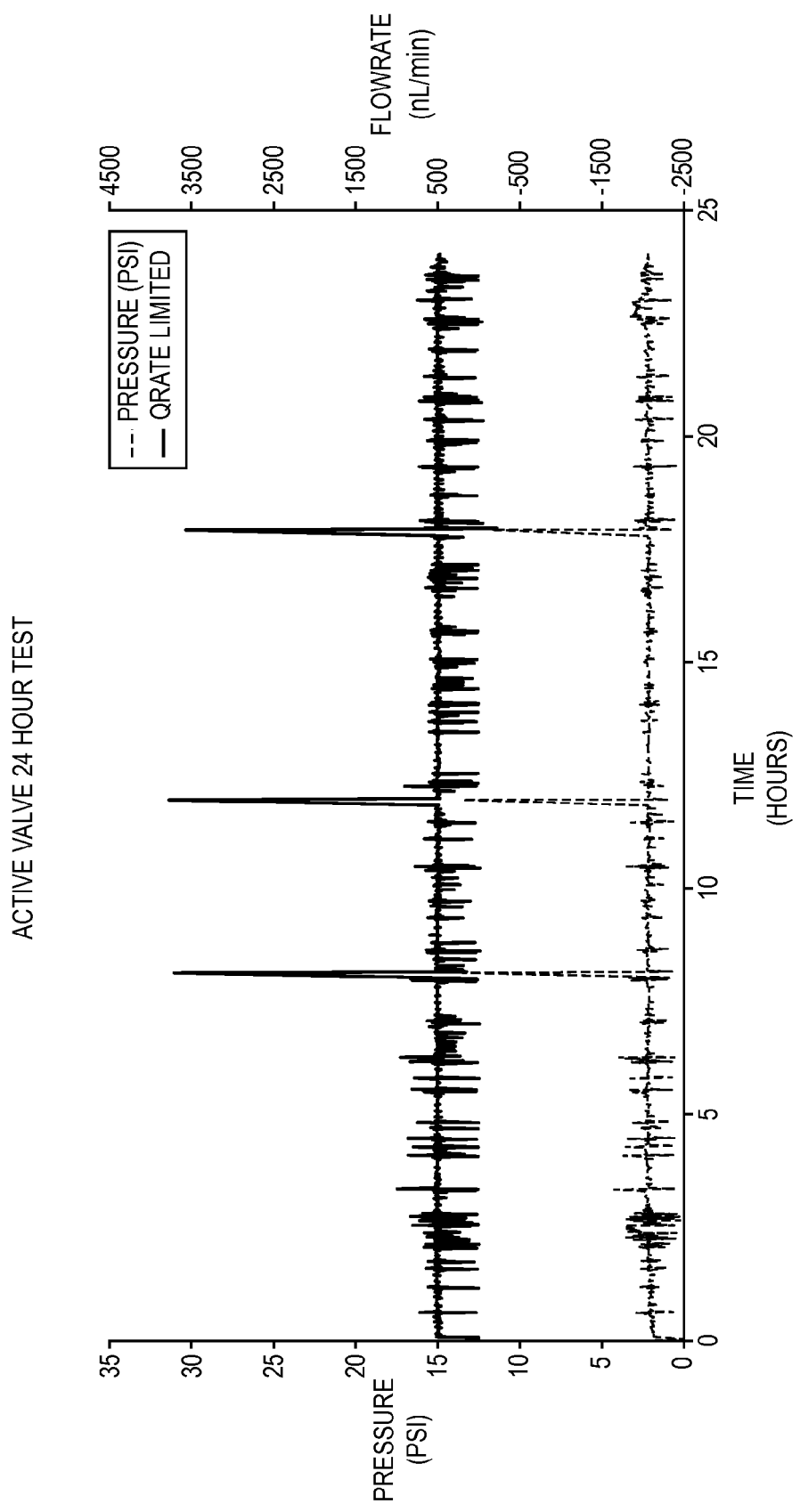
FIG. 17 is a diagram illustrating a 24 h period of basal and bolus delivery with a drug pump device in accordance with various embodiments.

For bolus delivery without background basal delivery, the pressure-relief mechanism is operated to allow the pressure in the pump chamber to go down to zero, causing the pump to completely stop drug delivery. Further, the electrolysis pump remains shut down, and electrolysis is not resumed until the next bolus delivery is due in accordance with the applicable delivery protocol. By contrast, for bolus delivery with background basal delivery, the pressure-relief mechanism is controlled to reduce the driving pressure until it reaches the target driving pressure for the background basal rate. Once this pressure is achieved, the pressure-relief mechanism is deactivated, and power to the electrolysis is started back up to maintain the target pressure level. To control the basal rate itself, a pressure sensor 1310 and feedback loop as described with respect to FIGS. 13A and 13B may be employed. Further, flow sensor readings may be used to increase the accuracy and reliability of the pump control scheme. Thus, a fully-functioned pump system (as shown in FIGS. 16A and 16B) may combine the feedback loops used with basal-only and bolus-only flow control to implement highly accurate delivery modes for continuous basal delivery, bolus delivery, and background basal plus multiple-bolus delivery. FIG. 17 illustrates the pump pressure and flow rate achieved over a 24-hour period with an exemplary insulin pump system including dual-sensor feedback and an active pressure-relief mechanism, showing a stable background basal delivery rate of 500 nl/min and three 10 µL bolus deliveries at times of 8, 12, and 18 hours, representing breakfast, lunch, and dinner, respectively.

Figure 18A:
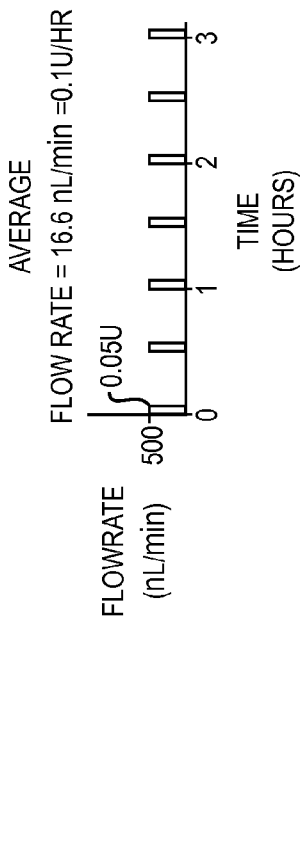
FIGS. 18A-18D are diagrams illustrating multi-bolus delivery protocols for low basal flow rates of 0.05 µl/h, 0.1 µl/h, 0.15 µl/h, and 0.2 µl/h, respectively.
Figure 18C:
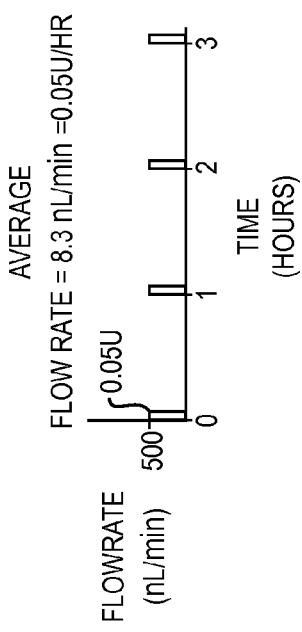
Figure 18B:
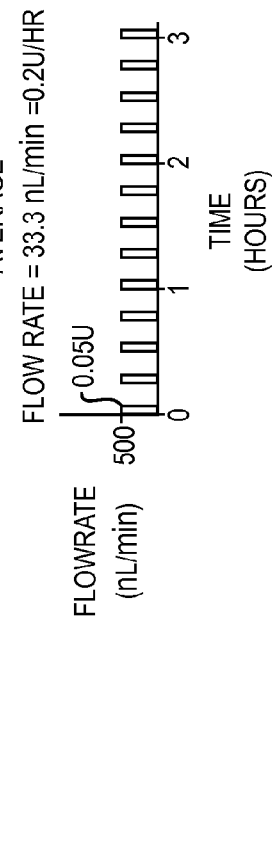
Figure 18D:
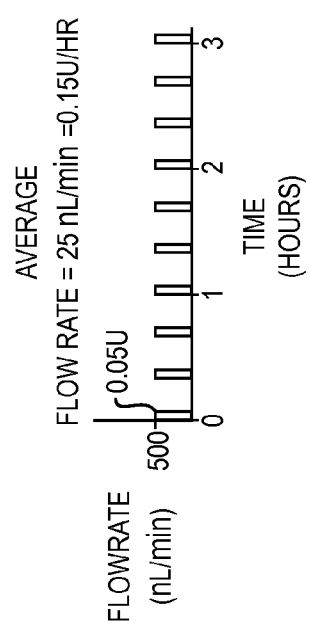

The bolus control scheme is also applicable to very low basal rates (e.g., with flow rates below 400 nl/min), at which continuous delivery becomes difficult due to the associated low driving pressure and resulting high impact of friction between the piston and vial. Low basal rates can be effected by discrete, fixed-volume (e.g., 8.3 nl) bolus deliveries at regular time intervals, which are adjusted to the desired average rate. For example, as illustrated in FIG. 18A, an average rate of 0.05 µl can be achieved with a single 8.3 nl injection per hour, whereas 2 µl/h require an 8.3 nl injection every 15 min, as shown in FIG. 18D.

The various feedback loops described above can generally be implemented in hardware (including analog and/or digital circuitry), software, or a combination of both. For example, signal voltages supplied by the sensors 1310, 1410 may first be converted into digital signals, which are then processed by the system controller 112 (which may, e.g., be a microcontroller or microprocessor) based on instructions stored in system memory 120 to compute the required electrolysis current. The pump driver 110 may receive a digital current control signal from the controller 112, convert it to an analog signal, and amplify the analog signal to provide the drive current to the electrodes. The instructions that implement the computational functionality may (but need not) be grouped into discrete modules, such as modules for comparing measured and target pressures or flow rates, arbitrating between different control parameters, computing flow rates from pressure values based on stored pump history data, integrating the flow rate to obtain delivered dosages, etc. The modules may generally be programmed in any suitable programming language, including, without limitation, high-level languages such as C, C++, C#, Ada, Basic, Cobra, Fortran, or Object Pascal, or low-level assembly languages; the choice of language may depend on the type of system controller or processor employed.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. For example, while this disclosure relates specifically to electrolysis pumps, certain aspects described herein, such as pump operation at high driving pressures or sensor-based feedback, may also be implemented in other types of pumps (e.g., electrochemical, osmotic, piezoelectric, pneumatic, of motor-driven pumps). Further, embodiments of the invention need not include all of the features or have all of the advantages described herein, but may possess any subset or combination of features and advantages. Accordingly, the described embodiments are to be considered in all respects as only illustrative and not restrictive.

What is claimed is:
1. A high-pressure drug pump device comprising:
a drug reservoir;

an exit member for fluidically connecting the reservoir with a drug injection site;

a flow restrictor for restricting fluid flow through the exit member, the flow restrictor having a flow resistance factor of at least $10^6 \, \mu l^{-1}$;

an electrolysis pump comprising a pump chamber in mechanical communication with the drug reservoir via an intervening displacement member, the electrolysis pump being operable to exert a pressure of at least 5 psi to drive the displacement member toward the exit member and thereby force therethrough fluid in the drug reservoir; and circuitry for operating the pump to generate a pressure of at least 5 psi, the circuitry and the flow restrictor cooperating to cause continuous fluid flow through the exit member at a constant flow rate in the range from about 400 nl/min to about 5 μl/min.

2. The device of claim 1, wherein the pump is operable to exert a pressure of at least 10 psi.

3. The device of claim 1, wherein the pump is operable to exert a pressure of at least 50 psi.

4. The device of claim 1, wherein the pump is operable to exert a pressure of at least 100 psi.

5. The device of claim 1, wherein the pump is operable to exert a pressure of at least 200 psi.

6. The device of claim 1, wherein the smallest inner diameter of the flow restrictor does not exceed 100 μm.

7. The device of claim 1, wherein the smallest inner diameter of the flow restrictor does not exceed 50 μm.

8. The device of claim 1, wherein the flow restrictor has a length in the range from about 1 cm to about 15 cm.

9. The device of claim 1, wherein the exit member comprises the flow restrictor.

10. The device of claim 1, wherein the exit member comprises a cannula connected to the flow restrictor.

11. The device of claim 1, wherein the flow resistance factor is within a range that results in a substantially linear relationship between the pump pressure and the flow rate of fluid flow through the exit member.

12. The device of claim 1, further comprising a pressure sensor disposed within the pump chamber for measuring a pressure therein.

13. The device of claim 12, wherein the circuitry for operating the pump is configured to adjust an electrolysis current supplied to electrolysis electrodes based on a comparison of the measured pressure with a target pressure so as to cause fluid flow at a target flow rate.

14. The device of claim 1, further comprising a flow sensor disposed within the exit member.

15. The device of claim 14, wherein the electrolysis pump further comprises control circuitry for adjusting an electrolysis current supplied to the electrodes based on a comparison of a flow-rate reading from the flow sensor with a target flow rate so as to cause fluid flow at a constant specified flow rate.

16. The device of claim 1, wherein the drug reservoir is formed inside a vial, the displacement member comprising a piston movably disposed within the vial.

17. The device of claim 16, wherein the electrolysis pump comprises an electronics module mounted to an end of the vial and forming the pump chamber between the piston and the electronics module.

18. The device of claim 17, wherein the pump chamber is sealed, at a wall formed by the electronics module, using an O-ring seated on top of a rim of the vial and within a circumferential recess of the electronics module.

19. The device of claim 17, wherein the electronics module is removable and reusable in a separate drug pump device.

20. The device of claim 1, further comprising a pressure sensor disposed within the pump chamber for measuring a pressure therein and a direct-measurement flow sensor disposed within the exit member, the control circuitry further being configured to (i) calculate a flow rate from the measured pressure, (ii) compare the calculated flow rate with the measured flow rate, and (iii) adjust an electrolysis current supplied to the electrodes based on the measured flow rate if it is within 5% of the calculated flow rate, and otherwise based on the calculated flow rate, whereby the pump is operated to generate a pressure causing continuous fluid flow through the exit member at a target flow rate.

* * * * *